US008465742B2

(12) United States Patent
Hall et al.

(10) Patent No.: US 8,465,742 B2
(45) Date of Patent: Jun. 18, 2013

(54) ANTI-COBRA TOXIN ANTIBODY FRAGMENTS AND METHOD OF PRODUCING A $V_H$H LIBRARY

(75) Inventors: J. Christopher Hall, Guelph (CA); Gabrielle Richard, Guleph (CA); Michael D. McLean, Guleph (CA)

(73) Assignee: University of Guelph, Guelph, Ontario (CA)

(*) Notice: Subject to any disclaimer, the term of this patent is extended or adjusted under 35 U.S.C. 154(b) by 0 days.

(21) Appl. No.: 13/132,161

(22) PCT Filed: Dec. 4, 2009

(86) PCT No.: PCT/CA2009/001760
§ 371 (c)(1),
(2), (4) Date: Sep. 21, 2011

(87) PCT Pub. No.: WO2010/063113
PCT Pub. Date: Jun. 10, 2010

(65) Prior Publication Data
US 2012/0003245 A1 Jan. 5, 2012

Related U.S. Application Data

(60) Provisional application No. 61/120,208, filed on Dec. 5, 2008, provisional application No. 61/145,667, filed on Jan. 19, 2009.

(51) Int. Cl.
*A61K 39/395* (2006.01)

(52) U.S. Cl.
USPC .................. 424/133.1; 424/135.1; 424/146.1; 530/387.3; 530/388.26; 435/7.1

(58) Field of Classification Search
None
See application file for complete search history.

(56) References Cited

U.S. PATENT DOCUMENTS 4,208,479 A * 6/1980 Zuk et al. ........................ 435/7.9
2006/0003412 A1 1/2006 Chamberlain et al.

FOREIGN PATENT DOCUMENTS

WO WO96/34103 A1 10/1996
WO WO2009/150539 A2 12/2009
WO WO2010/004432 A1 1/2010

OTHER PUBLICATIONS

Stewart et al., Toxicon. Apr. 2007;49(5):699-709. Epub Nov. 30, 2006.*
Janeway et al., Immunobiology, 3rd edition, 19097, Garland Press, pp. 3:1-3:11.*
Rudikoff et al., Proc Natl Acad Sci U S A. Mar. 1982;79(6):1979-83.*
Ghahroudi, M. et al., "Selection and identification of single domain antibody fragments from camel heavy-chain antibodies," FEBS Letters Sep. 15, 1997; 414(3): 521-526.*
Muyldermans S, et al., Trends Biochem Sci. Apr. 2001;26(4):230-5.*
Muyldermans S., J Biotechnol. Jun. 2001;74(4):277-302.*
Hmila, I. et al., "VHH, bivalent domains and chimeric Heavy chain-only antibodies with high neutralizing efficacy for scorpion toxin Aahl", Molecular Immunology, Aug. 2008, vol. 45, No. 14, p. 3847-3856.
Koch-Nolte, F. et al. "Single domain antibodies from llama effectively and specifically block T cell ecto-ADP-ribosyltransferase ART2.2 in vivo". FASEB Journal, Nov. 2007, vol. 21, No. 13, p. 3490-3498.
Stewart, C.S. et al., "Isolation, characterization and pentamerization of alpha-cobrotoxin specific single-domain antibodies froma naive phage display library: Preliminary findings for antivenom development". Toxicon. Apr. 2007, vol. 49, p. 699-700.

* cited by examiner

*Primary Examiner* — Michael Szperka
(74) *Attorney, Agent, or Firm* — Bereskin & Parr LLP/S.E.N.C.R.L., s.r.l.; Micheline Gravelle

(57) ABSTRACT

A method of constructing a $V_H$H library from an immunized camelid, using whole venom or an extract thereof There is also provided $V_H$H antibody fragments isolated from a library produced in hyperimmunized llama These $V_H$H antibody fragments were sequenced, and specifically bind α-cobratoxin.

15 Claims, 5 Drawing Sheets

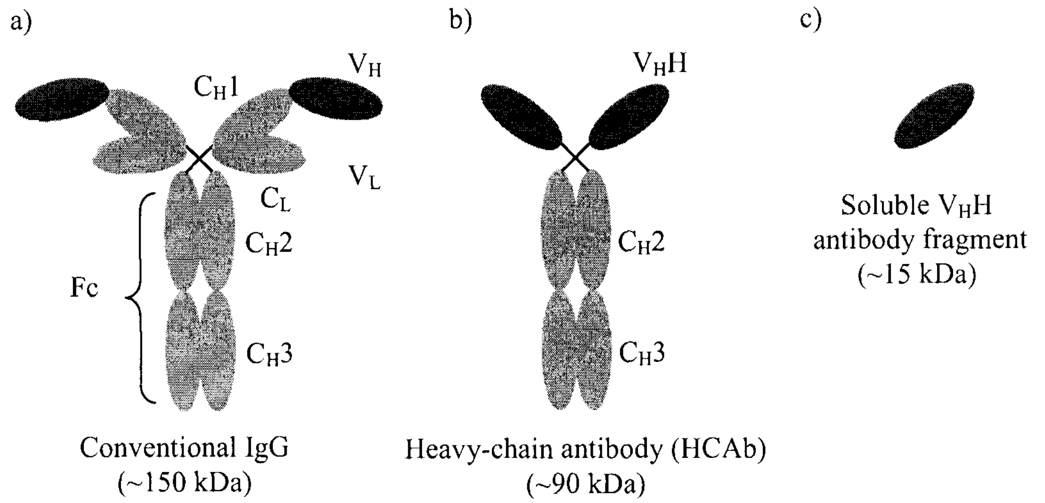
Figure 1. Schematic representation of a conventional IgG, a camelid heavy-chain antibody (HCAb) and a HCAb variable domain ($V_HH$)
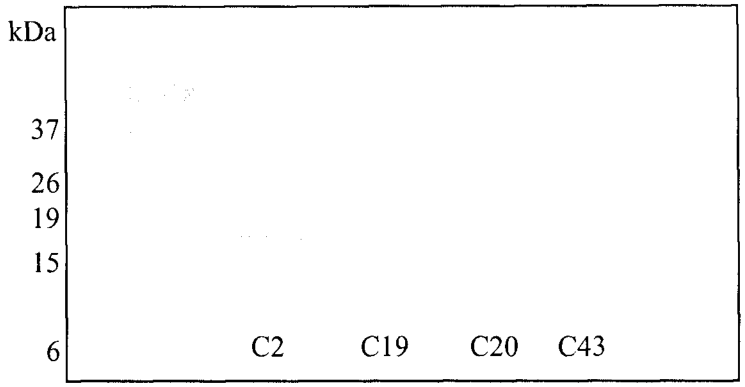
Figure 2. Western blot of $V_HH$ C2, C19, C20 and C43 purified from the periplasmic fractions of *E coli* using IMAC. $V_HHs$ were detected with anti-penta His mAb and goat anti-mouse mAb conjugated to alkaline phosphatase.

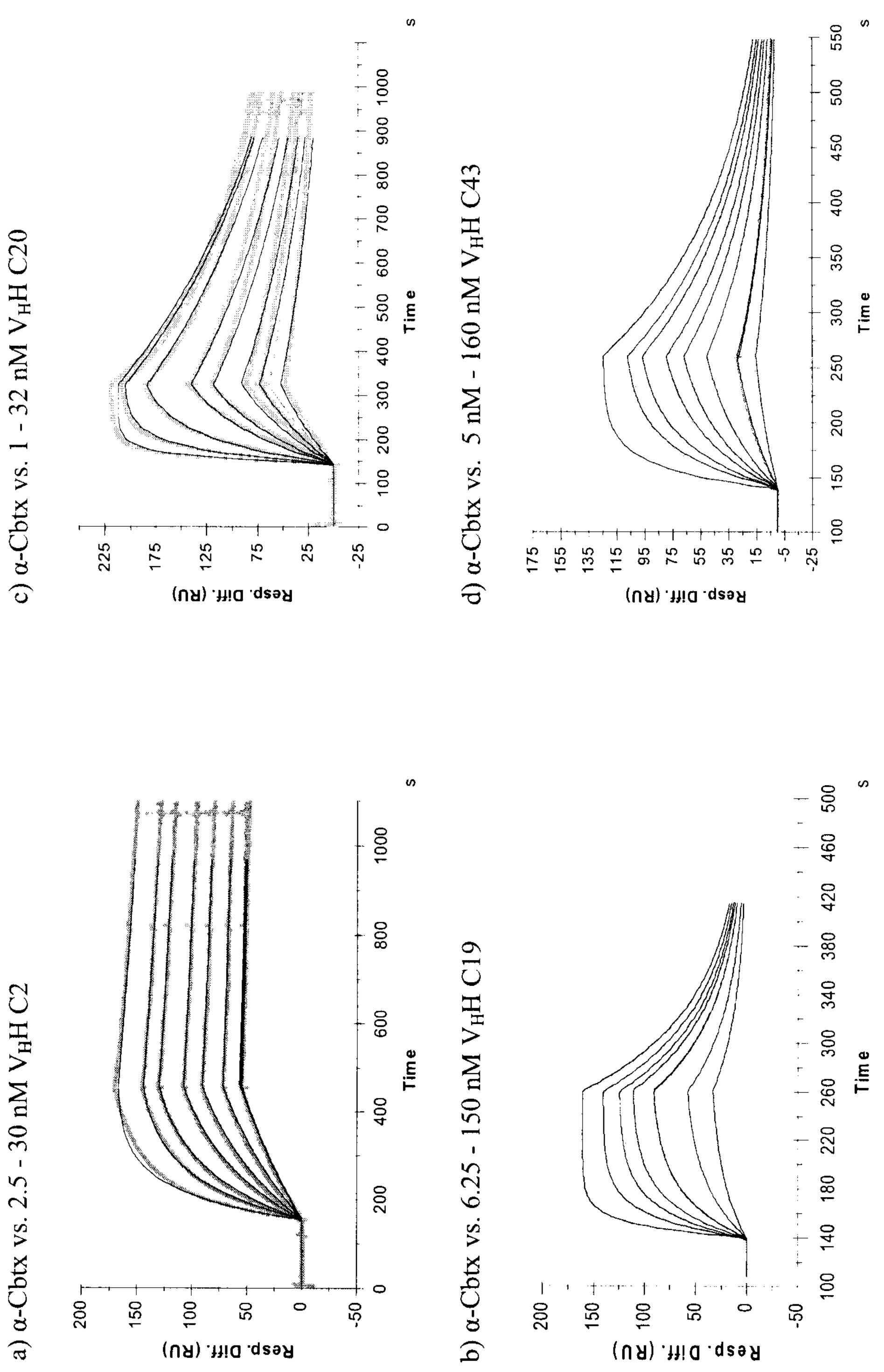
Figure 3. Surface plasmon resonance analysis of immobilized α-Cbtx vs. anti-α-Cbtx $V_H$H clones a) C2, b) C19, c) C20, and d) C43.

a) 600 nM C19 followed by 2 μM C43, 500 nM C20 and 1 μM C2
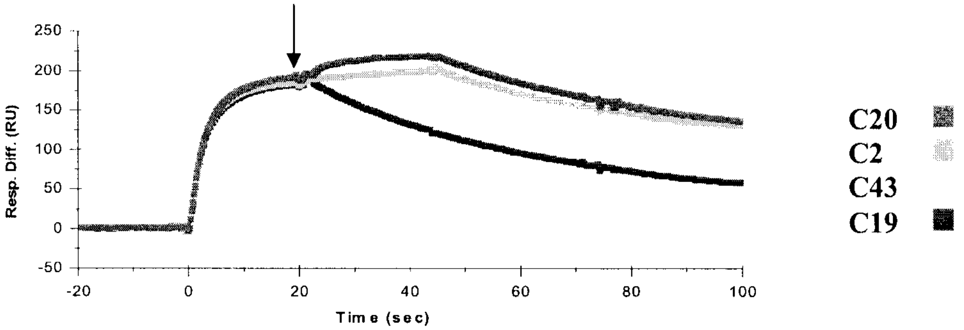
b) 2 μM C43 followed by 600 nM C19, 500 nM C20 and 1 μM C2
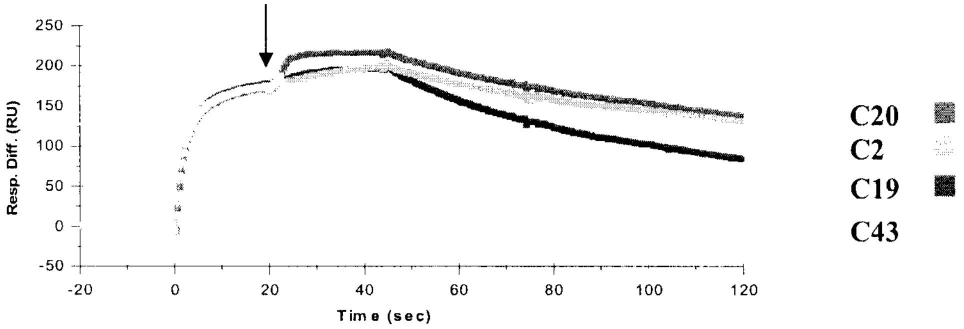
Figure 4. Epitope competition using surface plasmon resonance. After saturation of α-Cbtx with a) C19 or b) C43, the three other $V_HH$ clones were individually injected (arrows). The increase in RU is directly proportional to the amount of binding to α-Cbtx.

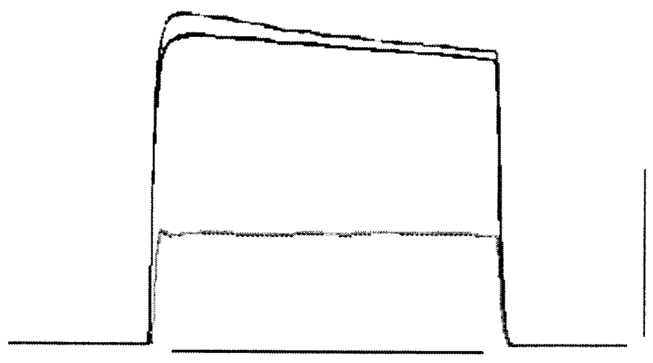

Figure 5. Attenuation of α-Cbtx inhibition of the tetanic response to phrenic nerve stimulation by $V_HH$ clone C2. Tetanic response in an untreated preparation (top), following α-Cbtx 50 nM *plus* $V_HH$ 100 nM (middle), and following 120 min later α-Cbtx 50 nM *without* $V_HH$ (bottom). α-Cbtx was co-incubated with $V_HH$ for 60 min at room temperature prior to adding to the tissue bath. The tetanic response to 100 Hz was measured and expressed as area/volts-sec with a) 3.46 mV sec, b) 3.47 mV sec, and c) 0.91 mV sec.

Cluster I

```
                FR1                       CDR1        FR2            CDR2              FR3                               CDR3               FR4

     1        10        20         30         40             50 a      60       70         80 abc          90          100|abcdefghi    110
C33  QVKLEESGGGLVQAGGSLRLSCIGS GDISSFNAMG WYRQVPGKQRELVA FISSGGRSKYTDSVKG RFTISGDNAKNTVYLQMIDLKPEDTAVYYCNA GSVVSYETGNYYEPSNY *GQGTQVTVSS
C46  *........................ .......... .............. ................ ................................ ................. W..........
C15  *........................ .......... .............. ................ ................................ ................. W..........
C7   ............*............ .......... .............. ................ ................................ ................. W..........
C13  *............P........... .......... .............. ................ ................................ ................. W..........
C19  ...........A............. .......... .............. ................ ................................ ................. W..........
C34  H.Q.V*................... .......... .............. ................ ................................ ................. W..........
C31  ............*.........A.. .S........ ....A......... ..T............. ..................N............. ...I..........D.. W..........
C20  .............P........V.. .S.....G.. .............. ................ ..........S.......N...........V. ...L..V.......D.. W..........
```

Cluster II

```
                FR1                       CDR1        FR2            CDR2              FR3                               CDR3            FR4

     1        10        20         30         40             50 a      60       70         80 abc          90          100|abcdef    110
C2   QVKLEESGGGLVLPGGSLRLSCAAS GSISSIYAMG WYRQAPGKQREVVA VITNGNSPNYADSVKG RFTISRDNAKNTVYLQMNSLKPEDTAVYYCNV EGVRYGDSWYDGDY WGQGTQVTVSS
C29  ..Q.V.......Q............ .......... .............. ................ ................................ ...........V.. ...........
C42  ............Q...........T .......... .............. ................ ................................ .............. ...........
C43  R...........QA.........V. ..TFDD..I. .............. ................ ................................ .............. ...........
```

Figure 6. Predicted amino acid sequence alignment of anti-α-Cbtx $V_HH$ binders isolated from the 3rd round of panning. The clones were categorized with either Cluster I or Cluster II based on their sequence homology. Residues are numbered according to the Kabat numbering system (Kabat and Wu, 1991). The dots in the sequences indicate amino acid identity that is the same as in C33 (Cluster I) or C2 (Cluster II). All clones belong to $V_HH$ Subfamily 2 (Harmsen *et al.*, 2000). An asterisk (*) represents an amber stop codon (TAG) mutation.

SEQUENCE LISTING

```
<160> NUMBER OF SEQ ID NOS: 33

<210> SEQ ID NO 1
<211> LENGTH: 122
<212> TYPE: PRT
<213> ORGANISM: Lama glama

<400> SEQUENCE: 1

Gln Val Lys Leu Glu Glu Ser Gly Gly Gly Leu Val Leu Pro Gly Gly
1               5                   10                  15

Ser Leu Arg Leu Ser Cys Ala Ala Ser Gly Ser Ile Ser Ser Ile Tyr
            20                  25                  30

Ala Met Gly Trp Tyr Arg Gln Ala Pro Gly Lys Gln Arg Glu Val Val
        35                  40                  45

Ala Val Ile Thr Asn Gly Asn Ser Pro Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Glu Gly Val Arg Tyr Gly Asp Ser Trp Tyr Asp Gly Asp Tyr Trp
            100                 105                 110

Gly Gln Gly Thr Gln Val Thr Val Ser Ser
        115                 120


<210> SEQ ID NO 2
<211> LENGTH: 125
<212> TYPE: PRT
<213> ORGANISM: Lama glama

<400> SEQUENCE: 2

Gln Val Lys Leu Glu Glu Ser Gly Gly Gly Leu Ala Gln Ala Gly Gly
1               5                   10                  15

Ser Leu Arg Leu Ser Cys Ile Gly Ser Gly Asp Ile Ser Ser Phe Asn
            20                  25                  30

Ala Met Gly Trp Tyr Arg Gln Val Pro Gly Lys Gln Arg Glu Leu Val
        35                  40                  45

Ala Phe Ile Ser Ser Gly Gly Arg Ser Lys Tyr Thr Asp Ser Val Lys
    50                  55                  60

Gly Arg Phe Thr Ile Ser Gly Asp Asn Ala Lys Asn Thr Val Tyr Leu
65                  70                  75                  80
```

-continued

```
Gln Met Ile Asp Leu Lys Pro Glu Asp Thr Ala Val Tyr Tyr Cys Asn
                85                  90                  95

Ala Gly Ser Val Val Ser Tyr Glu Thr Gly Asn Tyr Tyr Glu Pro Ser
            100                 105                 110

Asn Tyr Trp Gly Gln Gly Thr Gln Val Thr Val Ser Ser
        115                 120                 125


<210> SEQ ID NO 3
<211> LENGTH: 125
<212> TYPE: PRT
<213> ORGANISM: Lama glama

<400> SEQUENCE: 3

Gln Val Lys Leu Glu Glu Ser Gly Gly Gly Leu Val Gln Pro Gly Gly
1               5                   10                  15

Ser Leu Arg Leu Ser Cys Val Gly Ser Gly Ser Ile Ser Ser Phe Asn
            20                  25                  30

Gly Met Gly Trp Tyr Arg Gln Val Pro Gly Lys Gln Arg Glu Leu Val
        35                  40                  45

Ala Phe Ile Ser Ser Gly Gly Arg Ser Lys Tyr Thr Asp Ser Val Lys
    50                  55                  60

Gly Arg Phe Thr Ile Ser Gly Asp Asn Ala Lys Ser Thr Val Tyr Leu
65                  70                  75                  80

Gln Met Ile Asn Leu Lys Pro Glu Asp Thr Ala Val Tyr Tyr Cys Asn
                85                  90                  95

Val Gly Ser Val Leu Ser Tyr Val Thr Gly Asn Tyr Tyr Glu Pro Ser
            100                 105                 110

Asp Tyr Trp Gly Gln Gly Thr Gln Val Thr Val Ser Ser
        115                 120                 125


<210> SEQ ID NO 4
<211> LENGTH: 122
<212> TYPE: PRT
<213> ORGANISM: Lama glama

<400> SEQUENCE: 4

Arg Val Lys Leu Glu Glu Ser Gly Gly Gly Leu Val Gln Ala Gly Gly
1               5                   10                  15

Ser Leu Arg Leu Ser Cys Ala Val Ser Gly Ser Thr Phe Asp Asp Tyr
            20                  25                  30

Ala Ile Gly Trp Tyr Arg Gln Ala Pro Gly Lys Gln Arg Glu Val Val
        35                  40                  45

Ala Val Ile Thr Asn Gly Asn Ser Pro Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Glu Gly Val Arg Tyr Gly Asp Ser Trp Tyr Asp Gly Asp Tyr Trp
            100                 105                 110

Gly Gln Gly Thr Gln Val Thr Val Ser Ser
        115                 120


<210> SEQ ID NO 5
<211> LENGTH: 10
<212> TYPE: PRT
<213> ORGANISM: Lama glama
```

<400> SEQUENCE: 5

Gly Ser Ile Ser Ser Ile Tyr Ala Met Gly
1 5 10

<210> SEQ ID NO 6
<211> LENGTH: 10
<212> TYPE: PRT
<213> ORGANISM: Lama glama

<400> SEQUENCE: 6

Gly Ser Thr Phe Asp Asp Tyr Ala Ile Gly
1 5 10

<210> SEQ ID NO 7
<211> LENGTH: 10
<212> TYPE: PRT
<213> ORGANISM: Lama glama

<400> SEQUENCE: 7

Gly Asp Ile Ser Ser Phe Asn Ala Met Gly
1 5 10

<210> SEQ ID NO 8
<211> LENGTH: 10
<212> TYPE: PRT
<213> ORGANISM: Lama glama

<400> SEQUENCE: 8

Gly Ser Ile Ser Ser Phe Asn Gly Met Gly
1 5 10

<210> SEQ ID NO 9
<211> LENGTH: 17
<212> TYPE: PRT
<213> ORGANISM: Lama glama

<400> SEQUENCE: 9

Val Ile Thr Asn Gly Asn Ser Pro Asn Tyr Ala Asp Ser Val Lys Gly
1 5 10 15

Arg

<210> SEQ ID NO 10
<211> LENGTH: 17
<212> TYPE: PRT
<213> ORGANISM: Lama glama

<400> SEQUENCE: 10

Phe Ile Ser Ser Gly Gly Arg Ser Lys Tyr Thr Asp Ser Val Lys Gly
1 5 10 15

Arg

<210> SEQ ID NO 11
<211> LENGTH: 14
<212> TYPE: PRT
<213> ORGANISM: Lama glama

<400> SEQUENCE: 11

Glu Gly Val Arg Tyr Gly Asp Ser Trp Tyr Asp Gly Asp Tyr
1 5 10

<210> SEQ ID NO 12
<211> LENGTH: 17
<212> TYPE: PRT
<213> ORGANISM: Lama glama

<400> SEQUENCE: 12

Gly Ser Val Val Ser Tyr Glu Thr Gly Asn Tyr Tyr Glu Pro Ser Asn
1 5 10 15

Tyr

<210> SEQ ID NO 13
<211> LENGTH: 17
<212> TYPE: PRT
<213> ORGANISM: Lama glama

<400> SEQUENCE: 13

Gly Ser Val Leu Ser Tyr Val Thr Gly Asn Tyr Tyr Glu Pro Ser Asp
1 5 10 15

Tyr

<210> SEQ ID NO 14
<211> LENGTH: 366
<212> TYPE: DNA
<213> ORGANISM: Lama glama

<400> SEQUENCE: 14
caggtaaagc tggaggagtc tgggggaggc ttggtgctgc ctgggggGtc tctgagactc 60
tcctgtgcag cctctggaag catctctagt atctatgcca tggctggta ccgccaggct 120 ccagggaagc agcgcgaagt ggtcgcagtt attactaatg gtaatagtcc aaactatgca 180
gactccgtga agggccgatt caccatctcc agagacaacg ccaagaacac ggtgtatttg 240
caaatgaaca gcctgaaacc tgaggacacg gccgtctatt actgtaatgt cgagggtgtt 300
cggtacggtg atagctggta cgatggtgac tactggggcc aggggaccca ggtcaccgtc 360
tcctca 366

<210> SEQ ID NO 15
<211> LENGTH: 375
<212> TYPE: DNA
<213> ORGANISM: Lama glama

<400> SEQUENCE: 15
caggtaaagc tggaggagtc tgggggaggt ttggcgcagg ctgggggGtc tctgagactc 60
tcctgtatag ggtctggaga catctccagc ttcaatgcca tgggctggta ccgccaggtt 120
ccagggaagc agcgcgaatt ggtcgcattt attagtagcg gtggtcgctc aaaatataca 180
gactccgtga agggccgatt caccatctcc ggagacaacg ccaagaacac ggtgtatctg 240
caaatgatcg acctgaaacc tgaggacaca gccgtctatt actgtaatgc aggttcggtg 300
gtatcatacg aaactggtaa ttactacgaa ccatctaact actggggcca ggggacccag 360
gtcaccgtct cctca 375

<210> SEQ ID NO 16
<211> LENGTH: 375
<212> TYPE: DNA
<213> ORGANISM: Lama glama

<400> SEQUENCE: 16
caggtaaagc tggaggagtc tgggggaggc ttggtgcagc ctgggggGtc tctgagactc 60
tcctgtgtag ggtctggaag catctccagc ttcaatggca tgggctggta ccgccaggtt 120
ccagggaagc agcgcgaatt ggtcgcattt atcagtagtg gtggtcgctc aaaatataca 180
gactccgtga agggccgatt caccatctcc ggagacaacg ccaagagcac ggtgtatctg 240

-continued caaatgatca acctgaaacc tgaggacaca gccgtctatt actgtaatgt cggttccgtg 300
ctatcatacg taactggtaa ttactacgaa ccatctgatt actggggcca ggggacccag 360
gtcaccgtct cctca 375

<210> SEQ ID NO 17
<211> LENGTH: 366
<212> TYPE: DNA
<213> ORGANISM: Lama glama

<400> SEQUENCE: 17
cgggtaaagc tggaggagtc tgggggaggc ttggtgcagg ctgggggtc tctgagactc 60 tcctgtgctg tctctggatc tactttcgat gattatgcca taggctggta ccgccaggct 120
ccagggaagc agcgcgaagt ggtcgcagtt attactaatg gtaatagtcc aaactatgca 180
gactccgtga agggccgatt caccatctcc agagacaacg ccaagaacac ggtgtatttg 240
caaatgaaca gcctgaaacc tgaggacacg gccgtctatt actgtaatgt cgagggtgtt 300
cggtacggtg atagctggta cgatggtgac tactggggcc aggggaccca ggtcaccgtc 360
tcctca 366

<210> SEQ ID NO 18
<211> LENGTH: 10
<212> TYPE: PRT
<213> ORGANISM: Lama glama

<400> SEQUENCE: 18

Asp Ser Val Lys Gly Arg Phe Thr Ile Ser
1 5 10

<210> SEQ ID NO 19
<211> LENGTH: 45
<212> TYPE: DNA
<213> ORGANISM: Artificial Sequence
<220> FEATURE:
<223> OTHER INFORMATION: Primer

<400> SEQUENCE: 19
gcccagccgg ccatggccsm kgtgcagctg gtggaktctg gggga 45

<210> SEQ ID NO 20
<211> LENGTH: 45
<212> TYPE: DNA
<213> ORGANISM: Artificial Sequence
<220> FEATURE:
<223> OTHER INFORMATION: Primer

<400> SEQUENCE: 20
gcccagccgg ccatggccca ggtaaagctg gaggagtctg gggga 45

<210> SEQ ID NO 21
<211> LENGTH: 45
<212> TYPE: DNA
<213> ORGANISM: Artificial Sequenc
<220> FEATURE:
<223> OTHER INFORMATION: Primer

<400> SEQUENCE: 21
gcccagccgg ccatggccca ggctcaggta cagctggtgg agtct 45

<210> SEQ ID NO 22
<211> LENGTH: 21
<212> TYPE: DNA

<213> ORGANISM: Artificial Sequence
<220> FEATURE:
<223> OTHER INFORMATION: Primer

<400> SEQUENCE: 22
cgccatcaag gtaccagttg a 21

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
ggggtacctg tcatccacgg accagctga 29

<210> SEQ ID NO 24
<211> LENGTH: 34
<212> TYPE: DNA
<213> ORGANISM: Artificial Sequence
<220> FEATURE:
<223> OTHER INFORMATION: Primer

<400> SEQUENCE: 24
catgtgtaga ctcgcggccc agccggccat ggcc 34

<210> SEQ ID NO 25
<211> LENGTH: 47
<212> TYPE: DNA
<213> ORGANISM: Artificial Sequence
<220> FEATURE:
<223> OTHER INFORMATION: Primer

<400> SEQUENCE: 25
catgtgtaga ttcctggccg gcctggcctg aggagacggt gacctgg 47

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
ccctcatagt taagcgtaac gatct 25

<210> SEQ ID NO 27
<211> LENGTH: 17
<212> TYPE: DNA
<213> ORGANISM: Artificial Sequence
<220> FEATURE:
<223> OTHER INFORMATION: Primer

<400> SEQUENCE: 27
caggaaacag ctatgac 17

<210> SEQ ID NO 28
<211> LENGTH: 13
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(9)
<223> OTHER INFORMATION: n is a, c, g, or t

<400> SEQUENCE: 28
ggccnnnnng gcc 13

<210> SEQ ID NO 29
<211> LENGTH: 17
<212> TYPE: PRT
<213> ORGANISM: Lama glama
<220> FEATURE:
<221> NAME/KEY: MISC_FEATURE
<222> LOCATION: (4)..(4)
<223> OTHER INFORMATION: Xaa = V, L or I
<220> FEATURE:
<221> NAME/KEY: MISC_FEATURE
<222> LOCATION: (7)..(7)
<223> OTHER INFORMATION: Xaa = E or V
<220> FEATURE:
<221> NAME/KEY: MISC_FEATURE
<222> LOCATION: (16)..(16)
<223> OTHER INFORMATION: Xaa = N or D

<400> SEQUENCE: 29

Gly Ser Val Xaa Ser Tyr Xaa Thr Gly Asn Tyr Tyr Glu Pro Ser Xaa
1 5 10 15

Tyr

<210> SEQ ID NO 30
<211> LENGTH: 15
<212> TYPE: PRT
<213> ORGANISM: Lama glama

<400> SEQUENCE: 30

Phe Ile Ser Ser Gly Gly Arg Ser Lys Tyr Thr Asp Ser Val Lys
1 5 10 15

<210> SEQ ID NO 31
<211> LENGTH: 10
<212> TYPE: PRT
<213> ORGANISM: Lama glama
<220> FEATURE:
<221> NAME/KEY: MISC_FEATURE
<222> LOCATION: (2)..(2)
<223> OTHER INFORMATION: Xaa = D or S
<220> FEATURE:
<221> NAME/KEY: MISC_FEATURE
<222> LOCATION: (8)..(8)
<223> OTHER INFORMATION: Xaa = A or G

<400> SEQUENCE: 31

Gly Xaa Ile Ser Ser Phe Asn Xaa Met Gly
1 5 10

<210> SEQ ID NO 32
<211> LENGTH: 14
<212> TYPE: PRT
<213> ORGANISM: Lama glama
<220> FEATURE:
<221> NAME/KEY: MISC_FEATURE
<222> LOCATION: (13)..(13)
<223> OTHER INFORMATION: Xaa= D or V

<400> SEQUENCE: 32

Glu Gly Val Arg Tyr Gly Asp Ser Trp Tyr Asp Gly Xaa Tyr
1 5 10

<210> SEQ ID NO 33
<211> LENGTH: 16
<212> TYPE: PRT
<213> ORGANISM: Lama glama

-continued

```
<400> SEQUENCE: 33

Val Ile Thr Asn Gly Asn Ser Pro Asn Tyr Ala Asp Ser Val Lys Gly
1               5                   10                  15
```

ANTI-COBRA TOXIN ANTIBODY FRAGMENTS AND METHOD OF PRODUCING A $V_H$H LIBRARY

The present application is a national phase entry application of PCT/CA2009/001760 which claims the benefit of U.S. provisional application Ser. No. 61/120,208, filed Dec. 5, 2008 (now abandoned) and U.S. provisional application Ser. No. 61/145,667, filed Jan. 19, 2009 (now abandoned), both of which are incorporated herein by reference in their entirety.

INCORPORATION OF SEQUENCE LISTING

A computer readable form of the Sequence Listing "20436-15_SequenceListing.txt" (16,384 bytes), submitted via EFS-WEB and created on May 27, 2011, is herein incorporated by reference.

FIELD

The disclosure relates to $V_H$H antibody fragments that bind to a toxin in venom and a recombinant $V_H$H library against venom.

BACKGROUND

Snake bite is a serious global public health problem, especially in tropical and subtropical countries (Chippaux 1998). It is estimated that over 5 million snake bite cases occur worldwide each year, of which 2.6 million cause envenomation, and about 125,000 of these result in death (Chippaux 2006). *Naja kaouthia* (Thai cobra), a member of the Elapidae family, is one of the most venomous and dangerous snakes of Thailand, causing the highest mortality and morbidity due to snake envenomation (Viravan et al. 1986).

Envenomation by *N. kaouthia* is usually manifested by neurotoxicity and extensive local tissue necrosis (Viravan et al. 1986). The most toxic component of *N. kaouthia* venom is α-cobratoxin, a low molecular weight (7.8 kDa) post-synaptic α-neurotoxin (Karlsson 1979 cited in Pratanaphon et al. 1997). α-Cobratoxin binds with high affinity and specificity to the nicotinic acetylcholine receptors (nAChRs) on post-synaptic membranes of skeletal muscles, thereby preventing the access of ACh to the receptor's binding pocket (Bourne et al. 2005). Consequently, neuromuscular transmission is blocked and symptoms of muscle flaccid paralysis result. Lethality is generally a result of respiratory failure (Minton 1990). The venom of *N. kaouthia* also contains several cytotoxins that exhibit cytotoxic activities on many cell types (Inoue et al. 1987). Phospholipases A2 and metalloproteinases are the main components of the venom responsible for local tissue necrosis (Gutierrez et al. 2000).

Antivenoms are currently the only specific treatment for snake bites. Conventional antivenoms are prepared by hyperimmunizing an animal, generally a horse, with snake venom to generate high affinity antibodies against the foreign snake toxins. Horse serum is collected, and whole IgG molecules (150 kDa) are purified and produced into $F(ab')_2$ antibody fragments (100 kDa) by pepsin digestion and/or Fab antibody fragments (50 kDa) by papain digestion (Lalloo and Theakston 2003). These antibody fragments can then be administered intravenously to an envenomed patient to neutralize the activity of the snake venom toxins. Systemic envenomation is generally treated efficaciously with antivenom; administration of antivenom rapidly neutralizes neurotoxicity caused by the action of post-synaptic neurotoxins (Warrell 1992 cited in Gutierrez et al. 2006). However, antivenoms are ineffective in treating local effects on tissues near the snake bite because of the rapid activity of the toxins at the local tissue, and the inability of antivenom immunoglobulin fragments to reach and penetrate deep tissues (Gutierrez et al. 1998). Although many survive envenomation, a large number of victims are left with chronic physical disability and psychological sequelae as a result of the cytotoxic components of the snake venom (Viravan et al. 1992).

Aside from conventional IgGs, camels and llamas have evolved unique heavy chain IgG immunoglobulins naturally devoid of light chains and the CH1 domains (Hamers-Casterman et al. 1993). The antigen binding sites of these heavy chain IgGs are composed of a single variable domain (called $V_H$Hs), and are the smallest natural antigen binding domain (15 kDa). $V_H$H antibody fragments have several properties that potentially would make them superior candidates for antivenom development over conventional antivenoms. They are relatively non-immunogenic, soluble, stable, and highly tissue penetrable (Arbabi Ghahroudi et al. 1997; Cortez-Retamozo et al. 2002 and 2004; Muruganandam et al., 2002). Owing to their low molecular mass, $V_H$H antibody fragments permeate tissue compartments more readily than conventional antibody fragments (Cortez-Retamozo et al., 2002 and 2004) and, therefore, may protect victims from the tissue-damaging effects of venom toxins. Furthermore, because of their small size and high homology to the human $V_H$3 gene family, $V_H$Hs may produce less adverse reactions in patients than conventional antivenoms (Vu at al., 1997). Furthermore, $V_H$H antibody fragments can easily be expressed and purified from *E. coli*/yeast expression systems, solving the current short supply and high cost crisis of antivenoms (Arbabi Ghahroudi et al. 1997; Frenken et al. 2000).

Recently, three $V_H$Hs specific for α-cobratoxin were isolated from a naïve (synthetic) llama phage display library (Stewart et al. 2007). However, the affinities of these $V_H$Hs were too low (in uM range) for therapeutic efficacy. Therefore, there is a need in the art to obtain higher affinity $V_H$Hs against venom such as snake venom.

SUMMARY

A phage-displayed $V_H$H library was constructed from a llama hyperimmunized with crude *Naja kaouthia* venom to obtain higher affinity binders to α-cobratoxin. After three rounds of panning against alpha-cobratoxin, 26 unique clones were determined by monoclonal phage ELISA and DNA sequencing. Analyses of predicted amino acid sequences suggest two major groups of antibodies. Surface plasmon resonance (SPR) analyses showed that 4 soluble anti-alpha-cobratoxin $V_H$Hs clones had dissociation constants ($K_D$) in the low nanomolar range (0.4-25 nanoM), and that these four $V_H$Hs bound to the same or overlapping epitopes on α-cobratoxin. An in vitro muscle twitch assay showed that $V_H$H C2 ($K_D$=0.4 nM) effectively neutralized the paralytic effects of α-cobratoxin at neuromuscular junctions. Thus the present inventors have generated and identified novel high affinity $V_H$H antibody fragments against snake neurotoxins useful as novel therapeutic agents for the treatment of snake envenomation. The inventors also identified the heavy chain complementarity determining regions (CDRs) of the $V_H$H antibody fragments disclosed herein. The inventors further compared the amino acid sequences of the $V_H$H antibody fragments disclosed herein and determined consensus sequences showing conserved regions.

Accordingly, in one embodiment, the disclosure provides a method of obtaining a $V_H$H library comprising:

(1) immunizing a camelid with whole venom or an extract thereof;

(2) isolating nucleic acid sequences encoding the variable heavy ($V_H$H) fragment from the immunized camelid; and (3) transforming a suitable host with the nucleic acid sequences to prepare a recombinant $V_H$H library comprising $V_H$H antibody fragments that can bind to one or more proteins in the venom.

In another embodiment, the disclosure provides an isolated $V_H$H antibody fragment that can bind to one or more proteins present in venom.

The isolated $V_H$H may be prepared by panning a recombinant $V_H$H library with one or more proteins or toxins from the venom and selecting $V_H$H fragments that bind thereto.

In another embodiment, the disclosure provides an isolated heavy chain complementarity determining region 1 (CDR1) comprising an amino acid sequence selected from SEQ ID NOS:5-8 and 31 or a variant thereof. In another embodiment, the disclosure provides an isolated heavy chain complementarity determining region 2 (CDR2) comprising an amino acid sequence selected from SEQ ID NOS:9-10, 18, 30 and 33 or a variant thereof. In another embodiment, the disclosure provides an isolated heavy chain complementarity determining region 3 (CDR3) comprising an amino acid sequence selected from SEQ ID NOS:11-13, 29 and 32 or a variant thereof.

Another aspect of the present disclosure provides an isolated $V_H$H antibody fragment comprising: one or more isolated CDR1 sequences selected from SEQ ID NOS:5-8 and 31; and/or one or more isolated CDR2 sequences selected from SEQ ID NOS:9-10, 18, 30 and 33; and/or one or more isolated CDR3 sequences selected from SEQ ID NOS:11-13, 29 and 32; or a variant thereof. In another embodiment, the disclosure provides an isolated $V_H$H antibody fragment comprising an amino acid sequence selected from SEQ ID NOS: 1-4 or a variant thereof.

Another aspect of the present disclosure is an isolated nucleic acid sequence encoding: the heavy chain complementarity determining region 1 (CDR1) comprising an amino acid sequence selected from SEQ ID NOS:5-8 and 31; and/or the heavy chain complementarity determining region 2 (CDR2) comprising an amino acid sequence selected from SEQ ID NOS:9-10, 18, 30 and 33; and/or the heavy chain complementarity determining region 3 (CDR3) comprising an amino acid sequence selected from SEQ ID NOS:11-13, 29 and 32; or a variant thereof.

The present disclosure also includes an isolated nucleic acid sequence encoding the $V_H$H antibody fragment comprising an amino acid sequence selected from SEQ ID NOS:1-4 or a variant thereof. Another embodiment of the present disclosure is an isolated nucleic acid sequence encoding the $V_H$H antibody fragment comprising a nucleic acid sequence selected from SEQ ID NOS:14-17 or a variant thereof.

In one embodiment, the CDRs and/or $V_H$H antibody fragments disclosed herein bind to one or more proteins in a venom.

The disclosure includes all uses of the isolated CDRs and/or $V_H$H fragments disclosed herein including their use in therapy to treat a subject exposed to a venom and/or to treat envenomation in a subject and/or to neutralize a venom in a subject exposed to the venom.

Another aspect of the present disclosure is a pharmaceutical composition comprising an effective amount of the CDRs and/or $V_H$H fragments disclosed herein with a diluent or carrier and uses of the pharmaceutical composition thereof.

The present disclosure also includes a kit comprising an effective amount of the $V_H$H fragments disclosed herein together with ancillary agents and instructions for the use thereof.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

FIG. 1; (a) Conventional IgG (cIgG), (b) Heavy-chain antibody (HCAb) of camelids, and (c) $V_H$H antibody fragment.

FIG. 2: Western blot analysis of soluble α-Cbtx $V_H$H clones.

FIG. 3: Surface plasmon resonance analysis of immobilized α-Cbtx v.s anti-α-Cbtx $V_H$H C2, C19, C20 and C43.

FIG. 4: Epitope competition using surface plasmon resonance. After saturation of α-Cbtx with C19 (a) or C43 (b), the other three $V_H$Hs were injected (arrows). An increase in RU indicates further binding to α-Cbtx.

FIG. 5: Attenuation of α-Cbtx inhibition of the tetanic response to phrenic nerve stimulation by $V_H$H. Tetanic response in an untreated preparation (top line), following α-Cbtx 50 nM plus $V_H$H 100 nM (middle line), and following 120 min later α-Cbtx 50 nM without $V_H$H (bottom line). Pretreatments were for 30 min. α-Cbtx was co-incubated with $V_H$H for 60 min at room temperature prior to adding to the tissue bath.

FIG. 6: Predicted amino acid sequence alignment of anti-α-Cbtx $V_H$H binders isolated from the 3rd round of panning. The clones were categorized with either Cluster I or Cluster II based on their sequence homology. Residues are numbered according to the Kabat numbering system (Kabat and Wu, 1991). The dots in the sequences indicate amino acid identity that is the same as in C33 (Cluster I) or C2 (Cluster II). All clones belong to $V_H$H Subfamily 2 (Harmsen et al., 2000). An asterisk (*) represents an amber stop codon (TAG) mutation.

DETAILED DESCRIPTION

As previously mentioned, the present inventors have constructed a $V_H$H library from a llama hyperimmunized with *N. kaouthia* venom and isolated $V_H$H clones with high affinity and specificity to α-cobratoxin by phage display technology. The isolated $V_H$H clones were shown to neutralize the toxin in an in vitro mouse muscle twitch assay.

I. $V_H$H Library

In one embodiment, the disclosure provides a method of obtaining a $V_H$H library comprising:

(1) immunizing a camelid with whole venom or an extract thereof;

(2) isolating nucleic acid sequences encoding the variable heavy fragment ($V_H$H) from the immunized camelid; and (3) transforming a suitable host with the nucleic acid sequences to prepare a recombinant $V_H$H library comprising $V_H$H antibody fragments that can bind to one or more proteins in the venom.

The term "$V_H$H" as used herein means the variable domain of a heavy chain antibody isolated from a camelid. A $V_H$H is shown schematically in FIGS. 1*b*) and *c*).

The term "camelid" as used herein means a member of the family Camelidae including, without limitation, llamas, camels, dromedaries, alpacas, vicunas and guanacos. In one embodiment, the camelid is a llama or a camel.

The term "venom" as used herein means a substance that is released from an animal in order to immobilize, kill or facilitate digestion of its prey. Venoms are comprised of a mixture of enzymes, toxins, proteins and other small molecules. Animals that release a venom include, without limitation, snakes, spiders, scorpions, centipedes, stinging insects (such as bees or wasps), fish (such as stingrays and sharks), jelly fish, gila monster and Mexican lizards. In a specific embodiment, the venom is a snake venom.

The term "extract" of venom includes one or more of the enzymes, toxins, proteins or small molecules present in the complete venom. Examples of components of snake venom can be found in Table 4.

The term "nucleic acid sequences" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The camelid can be immunized with the venom or extract thereof at least once, although in one embodiment at least one booster immunization is given. For the initial immunization, the camelid may be injected at more than one site, or may be injected at two sites, or alternatively, may be injected at three sites. After each immunization regime, the antibody titer will be checked. Immunization will continue until antibody titer levels reach a plateau indicating the animal is hyperimmunized.

Once the desired antibody titer is reached, nucleic acid molecules, for example mRNA can be purified from lymphocytes of the hyperimmunized camelid. The mRNA transcripts can be reverse transcribed into a library of cDNA. From this library, $V_H$H DNA fragments, encoding the variable heavy fragment of the heavy-chain antibody, can be PCR amplified using 5'-forward and 3'-reverse primers complementary to ends of the $V_H$H domain, making a repertoire of $V_H$H genes. In order to clone these $V_H$H fragments into a phage vector, restriction sites can be introduced by PCR, for example using primers with Sfi I restriction sites flanking the $V_H$H sequence. After digestion with appropriate nuclease, the repertoire of $V_H$H fragments will be ligated with phage vector and transformed into competent host strain by electroporation. The host can be any suitable host including, without limitation, bacteria, yeast, plant cells and animal cells. In one embodiment, the host is a bacteria such as *E. coli.*

The term "primer" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

The term "complementary" refers to nucleic acid sequences capable of base-pairing according to the standard Watson-Crick complementary rules, or being capable of hybridizing to a particular nucleic acid segment under stringent conditions.

The phage-display library can be used to select $V_H$H antibody fragments that bind, with high affinity and specificity, to venom toxins. In this process, transformants harboring recombinant phage vector can be infected with M13 helper phage K07 (KM13) to produce a population of phage particles, each displaying a unique $V_H$H antibody fragment. $V_H$H clones specific for a particular toxin in the venom may be selected. In one embodiment, the library may be panned against several venom toxins. For example, phage particles may be panned against both immobilized α-cobratoxin and an immobilized mixture of crude venom toxins, separately. Phage particles carrying $V_H$H antibody fragments specific for the antigen will bind, and unbound phages will be washed away. Bound phages will be eluted, propagated in *E. coli* by helper phage infection, and used for the next round of panning. Each consecutive round of panning should enrich the antigen-binding specificity of clones. Generally, three to four rounds of panning are performed to select antibody fragments with desired affinity. The disclosure includes all $V_H$H antibody fragments isolated from the library disclosed herein. In one embodiment, the $V_H$H antibody fragment isolated from the library can bind to one or more proteins and/or toxins present in a venom. In another embodiment, the venom is a snake venom. In yet another embodiment, the $V_H$H antibody fragment isolated from the library binds to α-cobratoxin.

II. Complementarity Determining Regions and $V_H$H Antibody Fragments

As mentioned above, the present inventors have identified novel high affinity $V_H$H antibody fragments. The nucleotide and amino acid sequences are shown in Table 5. The inventors also identified the heavy chain complementarity determining regions (CDRs) of the $V_H$H antibody fragments (See Table 2), and also determined a consensus sequence showing a conserved region of the $V_H$H antibody fragments disclosed herein (See Table 7). The inventors analyzed the amino acid sequence alignment of $V_H$H antibody fragment clones isolated after the $3^{rd}$ round of panning, which were categorized as Cluster I or Cluster II based on their sequence homology, and further identified consensus motifs for CDR1, CDR2 and CDR3 in Clusters I and II (see FIG. 6).

Accordingly, in one embodiment, the disclosure provides an isolated heavy chain complementarity determining region 1 (CDR1) comprising the amino acid sequence: GSISSIYAMG (SEQ ID NO:5); GSTFDDYAIG (SEQ ID NO:6); GDISSFNAMG (SEQ ID NO:7); or GSISSFNGMG (SEQ ID NO:8); an isolated heavy chain CDR2 comprising the amino acid sequence: VITNGNSPNYADSVKGR (SEQ ID NO:9); or FISSGGRSKYTDSVKGR (SEQ ID NO:10); and an isolated heavy chain CDR3 comprising the amino acid sequence: EGVRYGDSWYDGDY (SEQ ID NO:11); GSWSYETGNYYEPSNY (SEQ ID NO:12); or GSVLSYVTGNYYEPSDY (SEQ ID NO:13). As noted above, the inventors have determined a consensus sequence for the $V_H$H antibody fragments disclosed herein. In particular, the consensus sequence comprises the amino acid sequence: DSVKGRFTIS (SEQ ID NO:18) and occurs within CDR2 of the $V_H$H antibody fragments disclosed herein. Accordingly, in one embodiment, CDR2 comprises the amino acid sequence in SEQ ID NO:18.

As noted above, the inventors determined consensus motifs for CDR1, CDR2 and CDR3 for clones categorized as Cluster I or II. In particular, the consensus motif for CDR1 in Cluster I comprises the amino acid sequence: G(D/S)ISSFN(A/G) MG) (SEQ ID NO:31); the consensus motif for CDR2 in Cluster I comprises the amino acid sequence: FISSGGR-SKYTDSVK; (SEQ ID NO:30); the consensus motif for CDR3 in Cluster I comprises the amino acid sequence: GSV (V/L/I)SY(E/V)TGNYYEPS(N/D)Y (SEQ ID NO:29); the consensus motif for CDR1 in Cluster II comprises the amino acid sequence: GSISSIYAMG (SEQ ID NO:5); the consensus motif for CDR2 in Cluster II comprises the amino acid sequence: VITNGNSPNYADSVKG (SEQ ID NO:33); and the consensus motif for CDR3 in Cluster II comprises the amino acid sequence: EGVRYGDSWYDG(D/V)Y (SEQ ID NO:32). Accordingly, in another embodiment, CDR1 comprises the amino acid sequence in SEQ ID NO:31; CDR2 comprises the amino acid sequence in SEQ ID NOS: 30 and 33; and CDR3 comprises the amino acid sequence in SEQ ID NOS: 29 and 32. In yet another embodiment of the present disclosure, the isolated CDR1, CDR2, and/or CDR3 comprising the amino acid sequences in SEQ ID NOS:5-8, and 31; SEQ ID NOS:9-10, 18, 30 and 33; and/or SEQ ID NOS:11-13, 29 and 32; respectively, can bind to one or more proteins present in venom.

The term "heavy chain variable region" as used herein refers to the variable domain of a heavy chain.

The term "heavy chain complementarity determining region" as used herein refers to regions of hypervariability within the heavy chain variable region of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus.

The term "amino acid" includes all of the naturally occurring amino acids as well as modified amino acids.

Additional aspects of the present disclosure are isolated $V_HH$ antibody fragments comprising one or more of the isolated heavy chain CDR1, CDR2 and/or CDR3 of the present disclosure (SEQ ID NOS:5-13, 18, and 29-33). In one embodiment, the isolated $V_HH$ antibody fragment comprises the isolated heavy chain CDR1, CDR2 and CDR3 selected from SEQ ID NOS:5, 9 and 11, respectively. In another embodiment, the isolated $V_HH$ antibody fragment comprises the isolated heavy chain CDR1, CDR2 and CDR3 selected from SEQ ID NOS:6, 9 and 11, respectively. In another embodiment, the isolated $V_HH$ antibody fragment comprises the isolated heavy chain CDR1, CDR2 and CDR3 selected from SEQ ID NOS:7, 10 and 12, respectively. In another embodiment, the isolated $V_HH$ antibody fragment comprises the isolated heavy chain CDR1, CDR2 and CDR3 selected from SEQ ID NOS:8, 10 and 13, respectively. In one embodiment, the isolated $V_HH$ antibody fragments comprising the isolated heavy chain CDR1, CDR2 and/or CDR3 of the present disclosure (SEQ ID NOS:5-13, 18, and 29-33) can bind to one or more proteins present in venom.

In another embodiment of the present disclosure, the $V_HH$ antibody fragment comprises the amino acid sequence: QVKLEESGGGLVLPGGSLRLSCAASG-SISSIYAMGWYRQAPGKQREVVAVI TNGNSPNYADS-VKGRFTISRDNAKNTVYLQMNSLKPED-TAVYYCNVEGVRY GDSWYDGDYWGQGTQVTVSS (SEQ ID NO:1). In another embodiment, the $V_HH$ antibody fragment comprises the amino acid sequence: QVKLEESGGGLAQAGGSLRLSCIGS-GDISSFNAMGWYRQVPGKQRELVAFI SSGGR-SKYTDSVKGRFTISGD-NAKNTVYLQMIDLKPEDTAVYYCNAGSVVS YETGNYYEPSNYWGQGTQVTVSS (SEQ ID NO:2). In another embodiment, the $V_HH$ antibody fragment comprises the amino acid sequence: QVKLEESGGGLVQPGGSL-RLSCVGSGSISSFNGMGWYRQVPGKQRELVAF ISSG-GRSKYTDSVKGRFTISGDNAK-STVYLQMINLKPEDTAVYYCNVGSVLS YVTGNYYEPSDYWGQGTQVTVSS (SEQ ID NO:3). In a further embodiment, the $V_HH$ antibody fragment comprises the amino acid sequence: RVKLEESGGGLVQAGGSL-RLSCAVSGSTFDDYAIGWYRQAPGKQREVVAVI TNGNSPNYADSVKGRFTISRD-NAKNTVYLQMNSLKPEDTAVYYCNVEGVRY GDSW-YDGDYWGQGTQVTVSS (SEQ ID NO:4). In another embodiment, the isolated $V_HH$ antibody fragments comprising the amino acid sequences selected from SEQ ID NOS:1-4 can bind to one or more proteins present in venom.

The present disclosure includes variants of the CDRs (i.e. variants of CDR1, CDR2 and/or CDR3) that can bind to one or more of the same proteins present in venom recognized by the CDRs (CDR1, CDR2 and/or CDR3) disclosed above.

The present disclosure also includes variants of the isolated $V_HH$ antibody fragments that can bind to one or more of the same proteins present in venom recognized by the $V_HH$ antibody fragments disclosed above.

The term "variant" as used herein includes modifications or chemical equivalents of the amino acid sequences disclosed herein that perform substantially the same function as the CDRs and/or $V_HH$ antibody fragments disclosed herein in substantially the same way. For example, variants of amino acid sequences disclosed herein include, without limitation, conservative amino acid substitutions. A "conservative amino acid substitution" as used herein, is one in which one amino acid residue is replaced with another amino acid residue without abolishing the binding properties of the CDRs and/or $V_HH$ antibody fragments. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

A person skilled in the art will appreciate that the present disclosure includes variants to the amino acid sequences of SEQ ID NOS:5-13, 18 and 1-4, including chemical equivalents to the sequences described in the present disclosure. Such equivalents include proteins that perform substantially the same function as the specific proteins disclosed herein in substantially the same way. For example, a functional variant of a CDR will be able to bind to the antigen recognized by the native CDR. For example, equivalents include, without limitation, conservative amino acid substitutions.

In one embodiment, the variant amino acid sequences of the heavy chain CDR1, CDR2 and/or CDR3 have at least 50%, or at least 60%, or at least 70%, or at least 80%, or at least 90%, or at least 95% sequence identity to SEQ ID NOS:5-8 and 31; 9-10, 18, 30 and 33; and 11-13, 29 and 32; respectively.

In another embodiment, the variant amino acid sequences of the $V_HH$ antibody fragments have at least 50%, or at least 60%, or at least 70%, or at least 80%, or at least 90%, or at least 95% sequence identity to SEQ ID NOS:1-4.

The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S, and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215: 403).

In one embodiment, the CDR1, CDR2 and CDR3 and/or $V_H$H antibody fragments disclosed herein can bind to one or more proteins present in snake venom. In another embodiment, the CDR1, CDR2 and CDR3 and/or $V_H$H antibody fragments disclosed herein can bind to α-cobratoxin present in the snake venom. In another embodiment, the CDR1, CDR2 and CDR3 and/or $V_H$H antibody fragments disclosed herein can bind to the same and/or overlapping epitopes on α-cobratoxin.

The CDRs (CDR1, CDR2 and CDR3) and/or $V_H$H antibody fragments described herein may be humanized in order to make them better tolerated for use in humans. For example, amino acid residues in the framework regions may be humanized by replacing them with amino acid residues and the human framework regions as long as the replacement does not impair the ability of the CDRs (CDR1, CDR2 and CDR3) and/or $V_H$H antibody fragments to bind to the toxin (Vincke C, Loris R, Saerens D, Martinez-Rodriguez S, Muyldermans S, Conrath K., "General strategy to humanize a camelid single-domain antibody and identification of a universal humanized nanobody scaffold", J Biol Chem. 2008).

The present disclosure also provides isolated nucleic acid sequences encoding: the heavy chain complementarity determining region 1 (CDR1) comprising the amino acid sequence: GSISSIYAMG (SEQ ID NO:5); GSTFDDYAIG (SEQ ID NO:6); GDISSFNAMG (SEQ ID NO:7); GSISSFNGMG (SEQ ID NO:8); or G(D/S)ISSFN(A/G)MG) (SEQ ID NO:31); the heavy chain CDR2 comprising the amino acid sequence: VITNGNSPNYADSVKGR (SEQ ID NO:9); FISSGGRSKYTDSVKGR (SEQ ID NO:10); DSVKGR (SEQ ID NO: 18); FISSGGRSKYTDSVK; (SEQ ID NO:30); or VITNGNSPNYADSVKG (SEQ ID NO:33); and the heavy chain CDR3 comprising the amino acid sequence: EGVRYGDSWYDGDY (SEQ ID NO:11); GSWSYETGNYYEPSNY (SEQ ID NO: 12); GSVLSYVTGNYYEPSDY (SEQ ID NO:13); GSV(V/L/I)SY(EN) TGNYYEPS(N/D)Y (SEQ ID NO:29); or EGVRYGDSWYDG(D/V)Y (SEQ ID NO:32).

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The present disclosure also provides an isolated nucleic acid sequence encoding the $V_H$H antibody fragments disclosed herein. In one embodiment, the isolated nucleic acid sequence encodes the $V_H$H antibody fragment comprising the amino acid sequence shown in SEQ ID NO:1. In another embodiment, the isolated nucleic acid sequence encodes the $V_H$H antibody fragment comprising the amino acid sequence shown in SEQ ID NO:2. In another embodiment, the isolated nucleic acid sequence encodes the $V_H$H antibody fragment comprising the amino acid sequence shown in SEQ ID NO:3. In another embodiment, the isolated nucleic acid sequence encodes the $V_H$H antibody fragment comprising the amino acid sequence shown in SEQ ID NO:4. In a further embodiment, the nucleic acid sequence encoding the $V_H$H antibody fragment comprises the nucleic acid sequence shown in SEQ ID NO:14. In a further embodiment, the nucleic acid sequence encoding the $V_H$H antibody fragment comprises the nucleic acid sequence shown in SEQ ID NO:15. In a further embodiment, the nucleic acid sequence encoding the $V_H$H antibody fragment comprises the nucleic acid sequence shown in SEQ ID NO:16. In an additional embodiment, the nucleic acid sequence encoding the $V_H$H antibody fragment comprises the nucleic acid sequence shown in SEQ ID NO:17.

The present disclosure also includes variants to the nucleic acid sequences that encode for the CDRs (CDR1, CDR2 and/or CDR3) disclosed herein. For example, the variants include nucleotide sequences that hybridize to the nucleic acid sequences encoding the CDRs (CDR1, CDR2 and/or CDR3) of the present disclosure under at least moderately stringent hybridization conditions.

The present disclosure also includes variants to the nucleic acid sequences that encode for the $V_H$H antibody fragments disclosed herein. For example, the variants include nucleotide sequences that hybridize to the nucleic acid sequences encoding the $V_H$H antibody fragments of the present disclosure under at least moderately stringent hybridization conditions.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature ($Tm=81.5°$ C.$-16.6$(Log 10 [Na+])+0.41(% (G+C)$-600/l$), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In one embodiment, stringent hybridization conditions are selected. By way of example the following conditions may be employed to achieve stringent hybridization: hybridization at 5× sodium chloride/sodium citrate (SSC)/5×Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

Accordingly, the present disclosure includes isolated nucleic acid sequences encoding variants of the CDRs and/or the $V_H$H antibody fragments discussed above.

Variant nucleic acid sequences include nucleic acid sequences that hybridize to the nucleic acid sequences encoding the amino acid sequences shown in SEQ ID NOS:5-13, 1-4, 18, and 29-33 and variants thereof under at least moderately stringent hybridization conditions.

III. Preparation of Proteins

A person skilled in the art will appreciate that the proteins of the present disclosure, such as the heavy complementarity determining regions, the $V_H$H antibody fragments, and the novel isolated proteins, such as $V_H$H antibody fragments isolated from the library described herein may be prepared in any of several ways, including for example, recombinant methods.

The term "isolated proteins" refers to a protein substantially free of cellular material and/or culture medium when produced by recombinant DNA techniques, or obtained from cultured cells or tissue samples, or of chemical precursors or other chemicals when chemically synthesized.

Accordingly, the nucleic acid molecules of the present disclosure may be incorporated in a known manner into an appropriate expression vector which ensures good expression of the proteins of the present disclosure. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the present disclosure and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The present disclosure therefore contemplates a recombinant expression vector of the present disclosure containing a nucleic acid molecule of the present disclosure, or a variant thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the present disclosure may also contain a selectable marker gene which facilitates the selection of host cells transformed or transfected with a recombinant molecule of the present disclosure. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the present disclosure and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the present disclosure. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the present disclosure may be expressed in yeast cells or mammalian cells. Other suitable host cells can be found in Goeddel, Gene Expression Technology: Methods in Enzymology 185, Academic Press, San Diego, Calif. (1991). In addition, the proteins of the present disclosure may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the present disclosure include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153:163 (1983), and Cullen et al. (Bio/Technology 5:369 (1987)).

Mammalian cells suitable for carrying out the present disclosure include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the present disclosure may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the present disclosure include cells and cell lines from *Bombyx, Trichoplusia* or *Spodotera* species. Baculovirus vectors available for expression of proteins in cultured insect cells (SF 9 cells) include the pAc series (Smith et al., Mol. Cell Biol. 3:2156-2165 (1983)) and the pVL series (Lucklow, V. A., and Summers, M. D., Virology 170:31-39 (1989)).

Alternatively, the proteins of the present disclosure may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The proteins of the present disclosure may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

Accordingly, the present disclosure provides a recombinant expression vector comprising the nucleic acid sequences that encode the proteins of the present disclosure, such as the heavy chain complementarity determining regions, the $V_H$H antibody fragments, and novel isolated proteins of the present disclosure, such as $V_H$H antibody fragments isolated from the library described herein. Further, the present disclosure provides a host cell comprising the nucleic acid sequences or recombinant expression vectors of the present disclosure.

IV. Methods and Uses

The present disclosure includes all methods and uses described herein of the CDRs (CDR1, CDR2 and/or CDR3) and/or $V_H$H antibody fragments described herein, including their use in therapeutic and diagnostic methods.

In one embodiment, the present disclosure provides a method of treating a subject that has been exposed to a venom comprising administering an effective amount of a CDR and/or $V_H$H antibody fragment to the subject. The disclosure also includes use of a CDR and/or $V_H$H antibody fragment to treat a subject that has been exposed to a venom. The disclosure also includes use of a CDR and/or $V_H$H antibody fragment in the manufacture of a medicament to treat a subject that has been exposed to a venom.

The "subject" can be any member of the animal kingdom, and in one embodiment is a human.

As used herein "exposed to a venom" means that a subject has been exposed to and/or has come into contact with a venom as defined herein. Venom exposure could occur, for example, by a bite, sting, or otherwise contact with a venomous animal (i.e. animal that releases a venom) and/or venomous substance.

In one embodiment, the present disclosure provides a method of treating envenomation in a subject comprising administering an effective amount of a CDR and/or $V_H$H antibody fragment to the subject. The disclosure also includes use of a CDR and/or $V_H$H antibody fragment to treat envenomation in a subject. The disclosure also includes use of a CDR and/or $V_H$H antibody fragment in the manufacture of a medicament to treat envenomation in a subject.

The term "envenomation" as used herein refers to neurotoxicity and/or neurotoxic effects and/or cytotoxicity that occur after a subject is exposed to a venom. As used herein "neurotoxicity" and/or "neurotoxic effects" includes, for example, paralytic effects of venom and/or blocking of neuromuscular transmission and/or muscle twitch and/or muscle flaccid paralysis and/or paralytic effects at neuromuscular junctions and/or effects of post-synaptic neurotoxins and/or respiratory failure. As used herein "cytotoxicity" includes, for example, cell death and/or cell damage and/or cell necrosis and/or tissue damage and/or tissue necrosis, including for example, local tissue necrosis and/or extensive local tissue necrosis.

"Treating envenomation" or "treat envenomation" as used herein means that neurotoxicity, neurotoxic effects and/or cytotoxicity are neutralized. As used herein "neutralized" means counteracting the effect of the venom and/or antidoting the venom, for example, by introducing an antibody and/or other therapeutic molecule that binds to the toxin at its active site and/or or at a protective epitope on the toxin molecule and/or by binding the toxin and mediating its clearance through the liver.

The present description also includes a method of neutralizing a venom in a subject that has been exposed to the venom comprising administering an effective amount of a CDR and/ or $V_HH$ antibody fragment to the subject. The disclosure also includes use of a CDR and/or $V_HH$ antibody fragment to neutralize a venom in a subject that has been exposed to the venom. The disclosure also includes use of a CDR and/or $V_HH$ antibody fragment in the manufacture of a medicament to neutralize a venom in a subject that has been exposed to the venom.

As used herein "neutralizing a venom" means without limitation counteracting the effects of a venom and/or antidoting the effects of a venom, for example, reducing the cytotoxicity and/or neurotoxicity and/or neurotoxic effects of the venom, which includes for example: a reduction in the paralytic effects of venom and/or a reduction in paralysis and/or a reduction in muscle twitch and/or a reduction in the blocking of neuromuscular transmission and/or a reduction in muscle flaccid paralysis and/or a reduction in the paralytic effects at neuromuscular junctions and/or a reduction of effects caused by post-synaptic neurotoxins and/or a reduction in respiratory failure and/or a reduction in cell death and/or cell damage and/or cell necrosis and/or tissue damage and/or tissue necrosis, including for example, local tissue necrosis and/or extensive local tissue necrosis.

The CDR and/or $V_HH$ antibody fragment is one that binds to a protein and/or toxin present in the venom to which the subject has been exposed. In one embodiment, in the methods and used described above, the subject is given several different CDRs and/or $V_HH$ antibody fragments disclosed herein, each one specific for a different protein and/or toxin present in the venom.

In another embodiment, in the methods and used described above, the CDRs and/or $V_HH$ antibody fragments bind to one or more proteins and/or toxins present in a venom. In another embodiment, in the methods and used described above, the CDRs and/or $V_HH$ antibody fragments bind to one or more proteins and/or toxins present in snake venom. In yet another embodiment, in the methods and used described above, the CDRs and/or $V_HH$ antibody fragments bind to α-cobratoxin present in the snake venom. In another embodiment, in the methods and used described above, the CDRs and/or $V_HH$ antibody fragments bind to the same and/or overlapping epitopes on α-cobratoxin.

V. Pharmaceutical Compositions

The present disclosure also includes a pharmaceutical composition comprising an effective amount of CDRs and/or $V_HH$ antibody fragment(s) of the disclosure in admixture with a suitable diluent or carrier.

Administration of an "effective amount" of the pharmaceutical compositions is defined as an amount effective, at dosages and for periods of time necessary to achieve the desired result. For example, a therapeutically active amount of a substance may vary according to factors such as the disease state, age, sex, and weight of the subject, and the ability of the CDR and/or $V_HH$ antibody fragment to elicit a desired response in the subject. Dosage regime may be adjusted to provide the optimum therapeutic response. For example, several divided doses may be administered daily or the dose may be proportionally reduced as indicated by the exigencies of the therapeutic situation.

The form of administration or use will depend on the nature and location of the venom. Suitable forms of administration include systemic (subcutaneous, intravenous, intramuscular), oral administration, inhalation, transdermal administration, topical application (such as topical cream or ointment, etc.) or by other methods known in the art.

Accordingly, the present disclosure provides a pharmaceutical composition for treating a subject exposed to a venom and/or treating envenomation in a subject and/or neutralizing a venom in a subject that has been exposed to the venom comprising one or more of the CDRs and/or $V_HH$ antibody fragments in admixture with a suitable diluent or carrier.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, $20^{th}$ ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. Immunoconjugate may be supplied, for example but not by way of limitation, as a lyophilized powder which is reconstituted with sterile water or saline prior to administration to the patient.

VI. Kits

The present disclosure also provides a kit comprising an effective amount of $V_HH$ antibody fragment(s) disclosed herein, together with instructions for the use thereof. In one embodiment, the use thereof includes treating a subject exposed to a venom and/or treating envenomation in a subject and/or neutralizing a venom in a subject that has been exposed to the venom. The kit can also include ancillary agents. For example, the kits can include instruments for injecting the $V_HH$ antibody fragment(s) disclosed herein into a subject, such as a syringe; vessels for storing or transporting the $V_HH$ antibody fragment(s) disclosed herein and/or a pharmaceutically suitable diluent or carrier.

The following non-limiting examples are illustrative of the present disclosure:

EXAMPLE 1

Materials and Methods

Immunization

A llama (*Lama glama*) was injected subcutaneously with increasing doses of crude *N. kaouthia* venom (Latoxan, France) every three weeks for a 15-week period.

The immunogen was administered subcutaneously at three different locations (0.25 mL/site) (i.e., one site near the neck and two in the hind quarters).

ca. 75 ml of blood was collected one week after each immunization for antibody specific titrations.

After collection of pre-immune sera (day −7), a one-year-old male llama (*Lama glama*) was immunized on days 0, 14, 35, 56, 75 and 103 with increasing amounts (i.e. 0.25, 0.5, 0.75, 1.0, 1.25 and 1.5 mg, respectively) of crude *N. kaouthia* venom. The venom [dissolved in phosphate buffered saline (PBS), pH 7.4] was emulsified in an equal volume of TiterMax™ Classic Adjuvant (Sigma-Aldrich, Oakville, ON, Canada) for the first three immunizations, and emulsified with an equal volume of Freund's Incomplete Adjuvant (Sigma-Aldrich, Oakville, ON, Canada) for subsequent immunization. The immunogen was administered subcutaneously at three different locations (0.25 mL/site) (i.e., one site near the neck and two in the hind quarters), which was similar to scheme described by Chotwiwatthanakun et al. (2001). Immune bleeds (~100 mL) were withdrawn from the jugular vein on days 21, 42, 63, 82 and 110. Serum was collected by centrifuging at 2,700×g for 10 min, aliquoted and stored at −20° C. until required for use. Whole llama blood was also collected, at days 82 and 110, in a glass vacuum bottle containing 1-2 mg/mL of EDTA (dipotassium salt) to prevent coagulation. Thereafter, peripheral blood leukocytes were recovered from 1.5 mL aliquots of this whole blood, lyzed as described in the QIAamp RNA Blood Mini Kit (Qiagen), and stored at −80° C. until required for RNA isolation.

Immune Response

Sera from days 42, 63, 82 and 110 were fractionated into HCAb and cIgG by Protein G and Protein A chromatography using a gradient pH elution (Hamers-Casterman et al., 1993).

HCAb immune response to α-Cbtx was monitored by enzyme-linked immunosorbant assay (ELISA).

The polyclonal immune responses against *N. kaouthia* venom components and α-Cbtx were monitored over the course of the llama immunization by indirect enzyme-linked immunosorbent assay (ELISA). Wells of a Reacti-Bind™ maleic anhydride-activated polystyrene microtitre plate (Pierce Biotechnology, Rockford, Ill.) were coated with 1 ug/mL of crude *N. kaouthia* venom or with 2.5 ug/mL of α-Cbtx (100 uL/well; PBS, pH 7.4) overnight (o/n) at 4° C. Negative background control wells were not coated with the antigen (PBS only). Wells were washed 3× with 200 uL of PBS (pH 7.4) to remove unbound antigen and then blocked o/n with 300 uL of 4% MPBS [4% (w/v) milk powder in PBS, pH 7.4]. Llama polyclonal serum from days −7, 21, 63, 110 were diluted by a serial two-fold dilution starting with a 1:50 dilution, added to the wells (100 uL/well), and incubated with gentle shaking at room temperature (RT). After 1.5 hr incubation, serum samples were removed and the wells were washed 3× with 200 uL of PBS-T (PBS plus 0.05% (v/v) Tween-20). Goat anti-llama IgG-heavy and light-chain conjugated to HRP (horse radish peroxidase) (Bethyl, lab Inc, 6 Montgomery, Calif.) diluted 1:2000 in 4% MPBS was added to the wells (100 uL/well) and incubated for 1 hr at RT with gentle shaking. Wells were washed 3× with 200 uL of PBS-T, and then developed with 100 μL/well of TMB substrate (3,3',5,5'-tetramethyl benzidine; Pierce, Rockford, Ill.). After 10 min, the reactions were neutralized with 1.5 M $H_2SO_4$. (100 μL/well) and the level of binding was determined spectrophotometrically at 450 nm.

After detecting a polyclonal immune response, a specific HCAb immune response against α-Cbtx was also determined. Llama sera were fractionated into HCAbs and convIgGs using protein G chromatography as described by Hamers-Casterman et al. (1993) with minor modifications. Four mL of sera from days 21 and 110 post-immunization and day −7 (pre-immune negative control) were dialyzed o/n against PBS (pH 7.4) using dialysis tubing with a 12-14 kDa MW cutoff. Dialyzed sera were diluted 10-fold in PBS (final volume 40 mL) and loaded onto a 5-mL protein G column (Hitrap, Pharmacia, Upsala, Sweden) using an ÄKTA FPLC system (GE Healthcare Bio-sciences AB, Uppsala, Sweden). After washing the column with PBS (pH 7.4), the HCAb fraction G1 was first eluted using 0.1M Citrate buffer (pH 3.5) and then the convIgG fraction G2 was eluted using 0.1M Glycine-HCl (pH 2.3). After elution, fractions were immediately neutralized with 1M Tris-HCl (pH 8.8), dialyzed o/n against PBS (pH 7.4), filtered through 0.22 μm and stored at 4° C. The purity of convIgG and HCAb fractions were determined by standard SDS-PAGE and Western blotting. Protein concentrations were spectrophotometrically measured at wavelength of 280 nm.

The HCAb immune response against α-Cbtx was assessed by indirect ELISA, as above, with the following exception: instead of using polyclonal serum, HCAb fractions G1 were titrated against microtitre plate-immobilized α-Cbtx (10 ug/mL).

$V_H$H Library Construction

To construct a $V_H$H library, total RNA was extracted from leukocytes of the $5^{th}$ bleed (Day-110).

After detecting a HCAb-positive immune response against α-Cbtx from fractionated sera, the $V_H$H library was constructed following the methods of Ghahroudi et al. (1997) with minor modifications. Total RNA was extracted from one aliquot (1.5 mL) of lyzed leukocytes (as above) from day 110 using the QIAamp RNA Blood Mini™ kit (Quiagen). Subsequently, this RNA (2 μg/8 uL) was used as template for the synthesis of the first strand cDNA using the First-Strand cDNA synthesis kit (Amersham Biosciences, Buckinghamshire, UK) and random hexamers [pd(N)6] as primers. Two cDNA synthesis reactions were carried out and pooled. The cDNA concentration was not quantified.

$V_H$H gene repertoire was amplified, cloned into pMED1 phagemid vector (Arbabi-Ghahroudi et al., 1997) and transferred into TG1 *E. coli.*

The first round of PCR reactions used framework-1 specific sense primers (MJ1.2.3 Back; Table 1) and CH2-specific anti-sense primers (CH2 and CH2B3; Table 1), thereby amplifying the $V_H$H-$C_H$2 and $V_H$-$C_H$1-$C_H$2 regions of HCAb and convIgG genes, respectively. To optimize the amplification of the $V_H$H gene segment, small-scale test PCR reactions were first carried out with various amounts of cDNA (0.5-3 uL) and $MgCl_2$ (0.5-3.0 mM). The optimal conditions for the amplification using the CH2 primer used 3.0 uL of cDNA and 1.5 mM $MgCl_2$. The PCR cycling parameters were as followed: 94° C. for 5 min (Taq hot start); 30 cycles of: 94° C. for 45 sec, 57° C. for 45 sec, 72° C. for 1.5 min; 72° C. for 7 min; 4° C. ∞.

The optimal conditions for the amplifications using the CH2B3 primer used 3.0 uL of cDNA and 0.5 mM $MgCl_2$. The PCR cycling parameters were as followed: 94° C. 5 min (Taq hot start); 6 cycles of: 94° C. for 45 sec, 57° C. for 45 sec, 54° C. for 45 sec, 72° C. for 1.5 min; 24 cycles of: 94° C. for 45 sec, 57° C. for 45 sec, 72° C. for 1.5 min; 72° C. for 7 min; 4° C. ∞.

Ten 50-μL PCR reactions of both primer sets (CH2 and CH2B3) were carried out with 5 pmol of the respective primers, 0.25 mM dNTPs and 2.5 units of Taq DNA polymerase (Hoffmann-La Roche Ltd.; Mississauga, ON). The 10 respective PCR products were pooled and electrophoresed on a 2% agarose gel to separate the $V_H$H-$C_H$2 (~600 bp) band from the $V_H$-$C_H$1-$C_H$2 (~900 bp) fragment. The $V_H$H-$C_H$2 (~600 bp) band was excised and purified using the Qiagen QIAquick Gel Extraction kit (QIAGEN Inc., Mississauga, ON, Canada).

Subsequently, the amplified $V_H$H-$C_H$2/-$C_H$2B3 products were used as template DNA for nested PCRs using primers specific for the extremities of framework-1 (MJ7; sense) and framework-4 (MJ8; anti-sense; Table 1), resulting in an amplified $V_H$H fragment without the $C_H$2 gene segment. These primers also introduced Sfi I restriction sites (5'-GGCCNNNN^NGGCC-3' (SEQ ID NO:28); See Table 1 underlined sequences) at the 5' and 3' end of the $V_H$H sequence. To optimize the $V_H$H gene amplification, small-scale test PCR reactions were performed with various amounts of $V_H$H-$C_H$2 or $V_H$H-$C_H$2B3 as template DNA (1-3 uL) and $MgCl_2$ (0.25-1.5 mM), and with different annealing temperatures. The optimal conditions for the amplifications of the $V_H$H gene segment used 5 ng of $V_H$H-$C_H$2 or 10 ng of $V_H$H-$C_H$2B3 amplicons as template DNA and 1.0 mM $MgSO_4$. Twenty 50-μL PCR reactions for both sets were done with 3.5 μmol of MJ7 and MJ8 primers, 0.25 mM dNTPs and 2.5 units of Taq DNA polymerase. An aliquot (~3 uL) from each PCR product was run on a 1% agarose gel to confirm the amplified product was of the correct size for a $V_H$H (~450 bp). All the PCR products were pooled and purified using MinElute spin columns (MinElute PCR Purification Kit; QIAGEN Inc., Mississauga, ON, Canada).

The $V_H$H gene repertoire (10 ug) was digested with Sfi I (New England Biolabs, Ipswich, USA) at 50° C. for 24 hr. After digestion, a small aliquot was analyzed on a 1% agarose gel to confirm it was the proper size for a $V_H$H fragment. The $V_H$H-Sfi I insert was purified using MinElute spin columns.

Twenty μg of pMED1 phagemid vector (Ghahroudi et al., 1997) were digested with Sfi I for 24 hr at 50° C., purified using QIAquick PCR purification kit, and double-digested with Pst I (Roche) and Xho I (Roche) for 5 hr at 37° C. The digested vector was purified with the QIAquick PCR purification kit and concentrated by standard ethanol DNA precipitation. Several test ligations/transformations were done to optimize the $V_H$H cloning (% insert) and transformation efficiencies. After optimization, twenty-seven small-scale ligation reactions were serially done with 200 ng vector, 75 ng of $V_H$H-Sfi I insert, 1 uL of T4 DNA ligase (Promega, Madison, Wis.), 1 uL of Buffer at 16° C. for 16 hr. The ligation material was pooled, purified using spin columns provided in the QIAquick PCR purification kit, and eluted in a total volume of 200 uL $ddH_2O$.

Four uL of the pMED1-$V_H$H ligated product were transformed into 50 uL of prepared electrocompentent *E. coli* TG1 at 1200 V, 25 pF and 200Ω using a Gene Pulser XcelI™ electroporator (Bio-Rad Laboratories, Mississauga, ON, Canada) and 0.1-cm electroporation cuvettes (Bio-Rad Laboratories, Mississauga, ON, Canada). Immediately after transformation, the cells were transferred to 1 mL of pre-warm SOC medium, and incubated with shaking for 1 hr at 37° C. A total of 50 transformations were done. After the 1 hr of incubation, the fifty 1-mL cultures were pooled. To determine the size of the library, a small aliquot (10 uL) of transformed cells was serially diluted ($10^{-4}$, $10^{-5}$ and $10^{-6}$) and plated onto 2×YT agar plates containing ampicillin (100 μg/mL) and 1% (w/v) glucose (2×YT/Amp/1% glucose). The culture was centrifuged at 3,000 g for 20 min and resuspended in 500 mL of 2×YT/Amp/2% glucose. The library was amplified o/n at 37° C. at 220 rpm. The next morning, the library was centrifuged as described above and resuspended in 100 mL of 2×YT/Amp/2% glucose with glycerol (30% final concentration). The amplified library was aliquoted (~$5.0\times10^9$ bacterial cells/aliquot; 3.5 mL), and stored at −80° C. until required for use.

Selection of α-Cbtx $V_H$H Binders

The $V_H$H phage-displayed library was panned three rounds against immobilized α-Cbtx.

For panning round 1, one well of a Reacti-Bind™ maleic anhydride-activated polystyrene microtitre plate (Pierce Biotechnology, Rockford, Ill.) was coated with sterile PBS (pH 7.4; 100 uL) and a second well was coated with 40 ug of α-Cbtx (diluted in sterile PBS, pH 7.4; 100 uL). For panning rounds 2 and 3, the coating concentration of α-Cbtx was decreased to 20 and 5 ug, respectively. After o/n incubated at 4° C., wells were washed 3× with 200 uL PBS and blocked with 300 uL of 4% MPBS at 37° C. for 2 hours. During this time, 100 uL of amplified phage and 100 uL of 8% MPBS (1:1 phage:blocking agent ratio) were combined in a 0.5 mL tube and pre-incubated with rotation for 1 hr at RT. After the blocking incubation was complete, the wells were washed 5× with PBS (300 uL). For subtractive panning of plastic binders, 100 uL of the pre-incubated phage were first incubated in the PBS coated well for 1 hr at 37° C. After incubation, the content of the well was transferred to the α-Cbtx coated well and incubated for 2 hr at 37° C. Unbound phages were removed by washing 5, 8 and 12× with PBST (200 uL) for panning rounds 1, 2 and 3, respectively, and then washed 2× with PBS (200 uL). To elute bound phages, 200 uL of 100 mM triethylamine (TEA) was added to the well and incubated at RT for 10 min. For the last 2 min of this incubation, the content of the well was stirred by pipetting up and down several times. Eluted phages were transferred to a microcentrifuge tube and vortexed with 400 uL of 1 M Tris-HCl (pH 7.4) to neutralize the TEA. Eluted phage (600 uL) were used to infect 1.4 mL of exponentially growing *E. coli* TG1 without shaking for 30 min at 37° C. After infection, a 10 uL aliquot of infected *E. coli* was used to make a serial dilution (from $10^{-2}$ to $10^{-6}$) to determine the phage titre (output). The remaining culture was spread on a 2×YT/Carb/1% glucose agar plate and incubated o/n at 32° C. The next morning, the cells were loosened from the plate using a plastic loop and 2 mL of 2×YT/Carb/15% glycerol. A 100 uL aliquot of these cells were inoculated into 50 mL of 2×YT/Carb/1% glucose for the production of phage for the next round of panning. (The remaining cells were stored at −80° C.). When the absorbance reading reached 0.4, $10^{11}$ pfu of M13KO7 helper phage was added to 10 mL of the *E. coli* culture. The growing of the culture and phage harvesting were performed as previously described in preparation for the next round of panning.

After 3 rounds of panning, 46 random clones were screened by monoclonal phage ELISA. Clones positive for binding to α-Cbtx were sequenced.

A total of 46 colonies (from the titre plate) from the third round of panning were screened for α-Cbtx binding by monoclonal phage ELISA. Colonies were grown in a 96-well culture plate (Corning Incorporated Life Sciences, Acton, Mass.) containing 100 uL/well of 2×YT supplemented with ampicillin (100 ug/mL) and 1% glucose. After incubation at 37° C. for 16 hr with shaking (220 rpm), 2 uL of each o/n culture was transferred into 200 uL of 2×YT supplemented with ampicillin and 1% glucose. Culture plates were incubated at 37° C. for 2 hr with shaking. After incubation, each culture was infected with $10^{10}$ helper phage (M13KO7) and incubated at 37° C. for 15 min without shaking and then for 1 hr with shaking (250 rpm). The culture plate was centrifuged at 1800 rpm for 10 min at 4° C., and the supernatant was carefully removed and discarded. Cell pellets were resuspended in 200 uL of 2×YT containing ampicillin (100 ug/mL) and kanamycin (50 ug/mL), and grown o/n with shaking (250 rpm) at 30° C. After centrifugation of the plate for 30 min as described above, 50 uL supernatant (which contain the $V_H$H-displayed phages) were collected and used for monoclonal phage ELISA.

Reacti-Bind™ maleic anhydride-activated polystyrene microtitre plates (Pierce Biotechnology, Rockford, Ill.) were coated with α-Cbtx (1 μg/mL), blocked with SuperBlock, and washed as described previously. Phage supernatant (50 μL) and SuperBlock (50 μL) were added to wells and incubated at 37° C. for 2 hr. Wells were washed and bound phage were detected as described above.

Clones with absorbance (450 nm) readings greater than 0.3 background were sequenced using the universal M13RP primer at the Laboratory Division Services (University of Guelph).

Soluble $V_H$H Protein Expression

Four unique anti-α-Cbtx $V_H$H clones (C2, C19, C20 and C43) were selected for soluble expression in *E. coli* HB2151 and purified from periplasm/cytoplasm extracts by IMAC using "HiTrap™ Chelating HP" column.

Preliminary expression and purification results showed that C2 and C43 clones expressed at low levels in pMED1 phagemid vector. Therefore, these $V_H$H coding sequences were subcloned into the Sfi I restriction sites of the expression vector pMED2 (kindly provided by Dr. Mehdi Arbabi-Ghahroudi). Proteins expressed from both pMED1 and pMED2 vectors contain a $His_6$ tag for purification.

For soluble expression of $V_H$Hs, purified recombinant C2-pMED2, C19-pMED1, C20-pMED1 and C43-pMED2 constructs were electroporated into *E. coli* strain HB2151, a non-suppressor strain. Single colonies were picked and transferred into 5 mL of 2×YT starter culture supplemented with 75 ug/mL carbicillin and 1% (w/v) glucose. Cultures were grown o/n at 37° C. while shaking at 220 rpm. For large-scale expression, 1 mL of starter culture was transferred into 1 L of 2×YT medium supplemented as described above and grown at 37° C. while shaking at 220 rpm until the $OD_{600}$ reached 0.6-0.7. The cell pellets were collected by centrifuging at 3,000 g and resuspended in 1 L of 2×YT medium supplemented with 0.1% (w/v) glucose and 75 μg/mL carbicillin. To induce soluble $V_H$H expression, IPTG (1 mM final conc.) was added to the cultures. Cultures were grown at 26° C. for 24 hr while shaking at 220 rpm. The induced cultures were centrifuged at 8,000 g for 15 min at 4° C. The harvested cells were resuspended in 100 mL of ice-cold lysis buffer (50 mM Tris-HCl at pH 8.0, 25 mM NaCl, 2 mM EDTA), and stored at −20° C. until needed for protein extraction.

$V_H$Hs were purified from the periplasmic fractions of *E. coli*. The induced cell pellets that were stored in lysis buffer (100 mL) were taken out of −20° C. freezer and 1 mL of 100 mM protease inhibitor phenylmethylsulphonyl fluoride (PMSF; 1 mM final conc.; Sigma-Aldrich, Oakville, ON) and 200 μL of 1 M dithiothreitol (DTT; 2 mM final conc.; Bioshop, Burlington, ON) were immediately added. The frozen suspension was thawed at RT with occasional shaking. To lyse the cells, 5 mL of freshly prepared lysozyme (100 μg/ml final conc. from 3 mg/ml aqueous solution; Roche, Indianapolis, Ind.) were added to the thawed cells. The suspension was incubated at RT for 30-50 min with occasional shaking. When the suspension became viscous 300 μL of DNase I (Sigma, Sigma-Aldrich, Oakville, ON; 15 units/μl stock in 1 M $MgCl_2$) was added and the lysate was incubated at RT until the suspension became watery (ca. 20-30 min). The lysate was centrifuged at 12,000 rpm for 20 min at 4° C. to separate the soluble and insoluble fractions. Centrifugation was repeated with the soluble fraction until it became clear. The soluble fraction which contained soluble $V_H$Hs were dialyzed o/n against PBS (pH 7.4) containing 1 mM EDTA. Samples were filtered through a 0.22 μm sterile filter (Millipore, Nepean, ON). $V_H$Hs were purified by standard immobilized metal affinity chromatography (IMAC) using a 5 mL HisTrap™ HP nickel affinity column (GE Healthcare Bio-sciences AB, Uppsala, Sweden).

Western blots were done to confirm expressions and purifications. The tagged $V_H$Hs were detected using anti-penta His monoclonal antibody (Qiagen, Mississauga, ON) diluted 5000 fold, and goat anti-mouse mAb conjugated to alkaline phosphatase (GAM-AP) diluted 5000 fold. Membranes were washed and developed with alkaline phosphatase substrate (1-Step NBT/BCIP; Pierce Biotechnology, Rockford, IL). Fractions containing $V_H$H were dialyzed o/n against SPR analysis buffer (10 mM HEPES, 150 mM NaCl, 3 mM EDTA; HBS-E) with a 3500 MW cutoff. Absorbancies were measured at 280 nm ($A_{280}$), and $V_H$H concentrations were estimated using an extinction coefficient based on the predicted amino acid sequence of each $V_H$Hs. The extinction coefficients for the purified clones were: C2, 2.089 (mg/mL); C19, 1.742 (mg/mL); C20, 1.744 (mg/mL); C43, 2.090 (mg/mL). The purified $V_H$Hs were stored at 4° C.

Affinity Measurements

Kinetic studies were performed for anti-α-Cbtx $V_H$H C2, C19, C20 and C43 using surface plasmon resonance (SPR).

Binding kinetic experiments were performed by SPR using a Biacore 3000 instrument (Biacore Inc., Piscataway, N.J.). Approximately 137 resonance units (RUs) of α-Cbtx were immobilized using standard amine coupling onto a research grade CM5 sensor chip (Biacore Inc.) in 10 mM acetate buffer. Prior to SPR analysis, $V_H$H samples purified from periplasmic fractions of *E. coli* (above) were subjected to Superdex 75 gel filtration chromatography (GE Healthcare) to isolate monomers from aggregates. $V_H$H monomers were passed over the sensor chip coated in HBS-EP running buffer [10 mM HEPES, pH 7.4, 150 mM NaCl, 3 mM EDTA, 0.005% surfactant P-20 (GE Healthcare)]. The four $V_H$Hs C2, C19, C20 and C43 were injected at concentrations ranging from 2.5 to 30 nM, 6.25 to 150 nM, 1 to 32 nM and 5 to 160 nM, respectively. All experiments were conducted at RT at a flow rate of 40 μL/min.

Epitope Competition

Epitope competition was performed using SPR to determine if the different $V_H$H clones target different, non-overlapping epitopes on α-Cbtx.

SPR analysis was used to determine if the α-Cbtx binders target the same or different epitopes. α-Cbtx was immobilized to the sensor chip as described above and then saturated with C19 or C43. After saturation, the ability of the second α-Cbtx binder to simultaneously bind the complex was monitored. To ensure the surface capacity (Rmax) was reached, α-Cbtx binders C2, C19, C20 and C43, were injected at 1 μM, 600 nM, 500 nM and 2 uM, respectively, as determined by the kinetic analysis results (Refer to "Affinity Measurements" section above). All assays were done at RT with a flow rate of 40 μL/min in HBS-EP running buffer. The RU signal created after the injection of the second α-Cbtx binder is proportional to the binding concentration of this $V_H$H.

Immobilized α-Cbtx was first saturated with either $V_H$H C19 or C43. After saturation was reached, another $V_H$H clone was applied and change in Response Difference was monitored. Increase in RD would indicate binding of second $V_H$H to a different epitope; no difference, binding to same epitope.

Comparison of Amino Acid Sequences for $V_H$H C2, C19, C20 and C43

Amino acid sequences for $V_H$H C2, C19, C20 and C43 were compared using the Basic Local Alignment Search Tool (BLAST) on the National Center for Biotechnology Information website.

A consensus sequence for the amino acid sequences of $V_H$H C2, C19, C20 and C43 was determined using the ClustalW tool at <http://www.ebi.ac.uk/Tools/clustalw2/index.html>.

In vitro α-Cbtx Neutralization Assay

A functional assay to assess the ability of $V_H$H C2 to neutralize the paralytic effects of α-Cbtx was investigated.

Methodology involved measurement of the force of contraction of a rat diaphragm muscle preparation stimulated at the phrenic nerve, in the presence of α-Cbtx with or without $V_H$H C2.

The diaphragm-phrenic nerve preparation is a widely used nerve-muscle preparation and was used to investigate the neutralization efficiencies of isolated $V_H$H clones to α-Cbtx at neuromuscular junctions. The assay was conducted in a manner similar to that described by Bulbring (1946). Briefly, the left hemi-diaphragm with the attached phrenic nerve was carefully excised from male Sprague Dawley Rats (175-250 g), and mounted on a special tissue holder immersed in a 50-mL Schuler organ bath containing Krebs-Henseleit solution. The incubation bath was maintained at 37° C. and fed constantly with 95% $O_2$-5% $CO_2$ by bubbling the gas through the solution. The preparation was attached via a thread suture to a Harvard isometric transducer for recording of contractions on a ®Biopac Systems MP150. The diaphragm contracted in response to "direct" stimulation using a set of parallel electrodes, which also serve to anchor the diaphragm, or to "indirect" stimulation via a second set of electrodes which stimulates the phrenic nerve to release neurotransmitter.

The phrenic nerve was continuously stimulated with supramaximal square wave pulses (0.25 ms) at a frequency of 0.1 Hz., followed by three 3-sec periods, at 30 sec intervals, at frequencies of 25, 50 and 100 Hz., to evoke twitch and tetanic reponses respectively, using a Grass® S88 stimulator. This protocol was repeated every 15 min in the presence or absence of neurotoxin with appropriate changes of bath fluid. In this case the tetanic response to 100 Hz was measured and expressed as area/volt-sec by the Biopac software program.

Purified $V_H$H C2 (100 nM) was pre-incubated with α-Cbtx (50 nM) for 60 min at RT prior to adding to the tissue bath. The assay was also performed with 50 nM of α-Cbtx (without $V_H$H) and served as a negative control. As a positive control, the tissue preparation was stimulated without the presence of α-Cbtx and $V_H$H C2.

Results

Immune Response

HCAb and cIgG fractions showed specific binding to both crude *N. kaouthia* venom and purified α-Cbtx (data not shown).

$V_H$H Library Construction

A $V_H$H phage-displayed library was constructed from the $5^{th}$ bleed.

A library of $4.2\times10^9$ clones with 84% $V_H$H-insert ratio was constructed.

Sequencing showed 100% diversity among 25 random clones.

Panning, Phage ELISA, and Sequence Results

Polyclonal phage ELISA using eluted phage from each round of panning showed a saturated signal with the $3^{rd}$ round of panning (data not shown).

Out of 46 random phage clones, 26 clones were positive for binding to α-cobratoxin by monoclonal phage ELISA.

Sequence analysis showed that 25 of these had unique sequences.

Analysis of the coding sequences and predicted amino acid compositions revealed that the $3^{rd}$ round of panning generated several unique α-Cbtx binders. Of all the clones sequenced, only two clones, C15 and C46, shared 100% identity. All other clones were unique with at least one different amino acid substitution. Many clones shared high identity as revealed by a multiple sequence alignment (MSA) of the predicted amino acid composition (FIG. 6). Moreover, based on the CDR homology and CDR3 length, two distinct groups of α-Cbtx binders are apparent, hereafter named Cluster I and Cluster II (see FIG. 6).

The nine clones (C33, C46, C15, C7, C13, C19, C34, C31, C20) that form Cluster I are characterized with a CDR3 length of 17 amino acid residues with the following consensus motif: GSV(V/L/I)SY(E/V)TGNYYEPS(N/D)Y (SEQ ID NO:29). All these binders have identical CDR2 regions (FISSGGRSKYTDSVK; (SEQ ID NO:30)), except for C31, which has a "T" at position 3 of SEQ ID NO:30, and a well conserved CDR1 (consensus motif: G(D/S)ISSFN(A/G)MG) (SEQ ID NO:31).

In contrast to Cluster I, clones that form Cluster II (C2, C29, C43, and C42) have a shorter CDR3 region with 14 amino acid residues, which has the following highly conserved consensus motif: EGVRYGDSWYDG(D/V)Y (SEQ ID NO:32). The clones among Cluster II share an identical CDR2 with the sequence VITNGNSPNYADSVKG (SEQ ID NO:33). Furthermore, all the clones from this group have a conserved CDR1 with the sequence GSISSIYAMG (SEQ ID NO:5), except C43 which has a unique CDR1.

Analyses of the predicted amino acid sequences suggest two major classes of antibodies (see Table 2. CDR3). Four α-Cbtx $V_H$H clones with high absorbance values as determined by ELISA (data not shown) were selected for further characterization; two from Cluster I (C19 and C20) and two from Cluster II (C2 and C43). As shown in Table 2, C2 and C43 differ by nine amino acid residues which are located in FR1 and CDR1. C19 and C20 differ by 10 amino acid residues which are located in different regions.

Full sequences for the CDR1, CDR2 and CDR3 are also shown in Table 2. Nucleotide sequences and predicted amino acid sequences for anti-α-cobratoxin $V_H$H C2, C19, C20 and C43 clones are shown in Table 5.

Comparison of Amino Acid Sequences for $V_H$H C2, C19, C20 and C43

The amino acid sequences of $V_H$H C2, C19, C20 and C43 was compared to determine the homology among the four sequences. The % identity and % similarity for $V_H$H C2, C19, C20 and C43 is shown in Table 6.

An overall comparison of the amino acid sequences for $V_H$H C2, C19, C20 and C30 was performed using Clustal W, and a consensus sequence for these four $V_H$Hs was determined. The consensus sequence shows conserved regions for $V_H$H C2, C19, C20 and C30, and is shown in Table 7.

Affinity Measurements

Surface plasmon resonance showed $K_D$ values ranged between 0.4-25 nM (FIG. 3 and Table 3).

Epitope Competition

It appears that the different $V_H$H clones target a region of overlapping or close together epitopes (FIG. 4).

In vitro α-Cbtx Neutralization Assay

C2 neutralizes the paralytic effects of α-Cbtx at neuromuscular junctions (FIG. 5).

Discussion

A positive HCAb immune response against α-Cbtx was generated using crude venom.

The $V_H$H library had a diversity 100% with a library size of $4.2\times10^9$ clones.

Four $V_H$H clones were characterized and had $K_D$s for α-Cbtx ranging from 0.4-25 nM.

These clones had a much higher affinity than those (2 to 3 uM) selected from a naïve phage-displayed $V_H$H library (Stewart et al., 2007).

In vitro muscle-twitch assay showed that anti-α-Cbtx $V_H$H C2 neutralizes the paralytic effects of alpha-cobratoxin.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Nucleotide sequence of primers used for the construction of the $V_H$H phage-displayed library. | |
|---|---|
| Primer name | Nucleotide sequence |
| MJ1 Back | 5'-GCCCAGCCGGCCATGGCCSMKGTGCAGCTGGTGGAKT CTGGGGGA-3' (SEQ ID NO: 19) |
| MJ2 Back | 5'-GCCCAGCCGGCCATGGCCCAGGTAAAGCTGGAGGAGT CTGGGGGA-3' (SEQ ID NO: 20) |
| MJ3 Back | 5'-GCCCAGCCGGCCATGGCCCAGGCTCAGGTACAGCTGG TGGAGTCT-3' (SEQ ID NO: 21) |
| CH2 | 5'-CGCCATCAAGGTACCAGTTGA-3' (SEQ ID NO: 22) |
| CH2B3 | 5'-GGGGTACCTGTCATCCACGGACCAGCTGA-3' (SEQ ID NO: 23) |

TABLE 1-continued

| Nucleotide sequence of primers used for the construction of the $V_H$H phage-displayed library. | |
|---|---|
| Primer name | Nucleotide sequence |
| MJ7 | 5'-CATGTGTAGACTCGCGGCCCAGCCGGCCATGGCC-3' (SEQ ID NO: 24) |
| MJ8 | 5'-CATGTGTAGATTCCTGGCCGGCCTGGCCTGAGGAGAC GGTGACCTGG-3' (SEQ ID NO: 25) |
| PN2 | 5'-CCCTCATAGTTAAGCGTAACGATCT-3' (SEQ ID NO: 26) |
| M13RP | 5'-CAGGAAACAGCTATGAC-3' (SEQ ID NO: 27) |

TABLE 2

Amino acid alignment of four selected anti-Cbtx $V_H$H clones. The dots in the sequence represent 100% identity with $V_H$H #2 and the dashes represent no amino acid.

| Clone | FR1 | CDR1 | FR2 | CDR2 |
|---|---|---|---|---|
| #2 | QVKLEESGGGLVLPGGSLRLSCAAS | GSISSIYAMG | WYRQAPGKQREVVA | VITNGNSPNYADSVKGR |
| #43 | R...........QA.........V. | ..TFDD..I. | .............. | ................. |
| #19 | ...........AQA........IG. | .DI..FN... | ....V......L.. | F.SS.GRSK.T...... |
| #20 | ............Q.........VG. | ..I..FNG.. | ....V......L.. | F.SS.GRSK.T...... |

| Clone | FR3 | CDR3 | FR4 | SEQ ID NO: |
|---|---|---|---|---|
| #2 | RFTISRDNAKNTVYLQMNSLKPEDTAVYYCNV | EGV---RYGDSWYDGDY | WGQGTQVTVSSG | 1 |
| #43 | ................................ | ...---........... | ............ | 2 |
| #19 | .....G..........ID.............A | GS.VSYET.NYYEPSN. | ............ | 3 |
| #20 | .....G...S......IN.............. | GS.LSYVT.NYYEPSD. | ............ | 4 |

| | CDR1 | SEQ ID NO: | CDR2 | SEQ ID NO: | CDR3 | SEQ ID NO: |
|---|---|---|---|---|---|---|
| C#2 | GSISSIYAMG | 5 | VITNGNSPNYADSVKGR | 9 | EGVRYGDSWYDGDY | 11 |
| C#43 | GSTFDDYAIG | 6 | VITNGNSPNYADSVKGR | 9 | EGVRYGDSWYDGDY | 11 |
| C#19 | GDISSFNAMG | 7 | FISSGGRSKYTDSVKGR | 10 | GSVVSYETGNYYEPSNY | 12 |
| C#20 | GSISSFNGMG | 8 | FISSGGRSKYTDSVKGR | 10 | GSVLSYVTGNYYEPSDY | 13 |

TABLE 3

Association ($k_{on}$) and dissociation ($k_{off}$) rate constants for the interaction of α-cobratoxin and $V_H$Hs during surface plasmon resonance.

| Clone | $K_{off}$ ($s^{-1}$) | $K_{on}$ ($M^{-1}s^{-1}$) | $K_D$ (nM) |
|---|---|---|---|
| #2 | $1.9 \times 10^{-4}$ | $5.2 \times 10^{5}$ | 0.4 |
| #43 | $6.8 \times 10^{-3}$ | $2.9 \times 10^{5}$ | 24 |
| #19 | $1.0 \times 10^{-2}$ | $5.8 \times 10^{5}$ | 25 |
| #20 | $1.7 \times 10^{-3}$ | $1.8 \times 10^{6}$ | 1 |

TABLE 4

Protein constituents of *Naja kaouthia* venom.

| Protein Name (Accession #) Synonyme Names | MW (Da) | Toxic Dose $LD_{50}$ | Function | References |
|---|---|---|---|---|
| α-Cobratoxin (P01391) | 7820 | 0.1 mg/kg i.v. | Inhibits neuromuscular transmission by binding to | Karlsson, 1973 |

TABLE 4-continued

Protein constituents of *Naja kaouthia* venom.

| Protein Name (Accession #) Synonyme Names | MW (Da) | Toxic Dose $LD_{50}$ | Function | References |
|---|---|---|---|---|
| Long neurotoxin 1, Neurotoxin 3, α-Cbtx | | | nicotinic acetylcholine receptors at neuromuscular junctions. | |
| Cobrotoxin (P60771) CBT, Short neurotoxin 1, NT1 | 9262 (precursor) | 0.325 mg/kg i.p. | As above | Meng et al., 2002 |
| Cobrotoxin II (P82849) CBT II, CBT2, Short neurotoxin 5 | 6862 | Unknown | As above | Cheng et al., 2000 |
| Cobrotoxin-b (P59275) CBT-b, Short neurotoxin 3, NT3 | 6944 | 400 mg/kg i.p. | As above | Meng et al., 2002; Cheng et al., 2000 |
| Cobrotoxin-c (P59276) CBT-c, NT2, Short neurotoxin 2 | 6859 | 80 mg/kg i.p. | As above | Meng et al., 2002; Cheng et al., 2000 |
| Short neurotoxin I (P14613) Toxin C-6 | 6983 | Unkown | As above | Chiou, S. H., et al., 1989 |
| Phospholipase A2 isozyme 1 (P00596) NnkPLA-I, CM-II | 16,271 | 10 mg/kg i.v., mouse | Catalyzes the hydrolysis of the acyl group attached to the 2-position of 3-sn-phosphoglycerides | Joubert and Taljaard, 1980a; Chuman et al., 2000 |
| Phospholipase A2 isozyme 2 (P00597) NnkPLA-II, CM-III | 16,016 | 4.4 mg/kg i.v., mouse | As above | Joubert and Taljaard, 1980a; Chuman et al., 2000 |
| Cytotoxin 1 (P60305) Cardiotoxin F-8, CTX1, CM-6 | 6701 | 1.3 mg/kg, i.v. | Cytolytic activity | Joubert and Taljaard, 1980b; Fryklund and Eaker, 1975; Ohkura et al, 1988 |
| Cytotoxin 2 (P01445) Cytotoxin CM-7A | 6745 | 1.2 mg/kg i.v. | As above | Joubert and Taljaard, 1980b |
| Cytotoxin 3 (P01446) Cytotoxin CM-7, CX3, CT3 | 6708 | 1.2 mg/kg i.v. | As above | Joubert and Taljaard, 1980b; Ohkura, et al., 1988 |
| Cytotoxin IV (P60303) | 6739 | 1.48 mg/kg i.p. | As above | Ohkura et al., 1988; Chiou et al., 1989 |
| Cytotoxin 5 (P24779) Cytotoxin II | 6646 | Unknown | As above | Ohkura et al., 1988 |
| Cytotoxin like basic protein (P14541) | 6977 | Unknown | Low cytotoxic activity | Inoue et al, 1987 |
| Hemorrhagic metalloproteinase-disintegrin kaouthiagin (P82942) | 44493 | Unknown | Cleaves the von Willebrand factor in humans, thereby inhibiting platelet aggregation during hemorrhages | Ito et al., 2001 |
| Cobra venom factor (Q91132) CVF. Complement C3 homolog | 149,000 | Unknown | Compliment-activating factor of venom | Eggertsen et al., 1981 Fritzinger et al., 1994; Kock et al., 2004 |
| Muscarinic toxin-like protein 1 (P82462) MTLP-1 | 7361 | Unknown | Binds weakly to muscarinic acetylcholine receptor | Kukhtina et al., 2000 |
| Muscarinic toxin-like protein 2 (P82463) MTLP-2 | 7293 | Unknown | As above | Kukhtina et al., 2000 |
| Muscarinic toxin-like protein 3 (P82464) MTLP-3 | 7615 | Unknown | As above | Kukhtina et al., 2000 |
| Weak toxin CM-9a (P25679) | 7438 | 82 mg/kg i.v. | Binds weakly to the nicotinic acetylcholine receptor | Joubert and Taljaard, 1980c cited in the Universal Protein Resource website (UniProt). |
| Weak tryptophan-containing neurotoxin (P82935) WTX | 7613 | Approximately 300 less potent than α-Cbtx and NT 2 | Binds weakly to the nicotinic acetylcholine receptor | Utkin et al., 2001 |
| Cysteine-rich venom protein 23 (P84808) CRVP-23k | 23621 | Non-toxic | Unknown | Osipov et al., 2005 |

TABLE 4-continued

| Protein constituents of *Naja kaouthia* venom. | | | | |
|---|---|---|---|---|
| Protein Name (Accession #) Synonyme Names | MW (Da) | Toxic Dose $LD_{50}$ | Function | References |
| Cysteine-rich venom protein 24 (P84803) CRVP-24k | 24080 | As above | As above | Osipov et al., 2005 |
| Cysteine-rich venom protein 25 (P84805) CRVP-25k | 24093 | As above | As above | Osipov et al., 2005 |

TABLE 5

Nucleotide and Amino Acid Sequences for Anti-α-cobratoxin $V_H$H C2, C19, C20 and C43.

Nucleotide Sequences $V_H$H C2

(SEQ ID NO: 14)

CAGGTAAAGCTGGAGGAGTCTGGGGGAGGCTTGGTGCTGCCTGGGGGGTCTCTGAGACTCTCCTGTGCA
GCCTCTGGAAGCATCTCTAGTATCTATGCCATGGGCTGGTACCGCCAGGCTCCAGGGAAGCAGCGCGAA
GTGGTCGCAGTTATTACTAATGGTAATAGTCCAAACTATGCAGACTCCGTGAAGGGCCGATTCACCATC
TCCAGAGACAACGCCAAGAACACGGTGTATTTGCAAATGAACAGCCTGAAACCTGAGGACACGGCCGTC
TATTACTGTAATGTCGAGGGTGTTCGGTACGGTGATAGCTGGTACGATGGTGACTACTGGGGCCAGGGG
ACCCAGGTCACCGTCTCCTCA $V_H$H C19

(SEQ ID NO: 15)

CAGGTAAAGCTGGAGGAGTCTGGGGGAGGTTTGGCGCAGGCTGGGGGGTCTCTGAGACTCTCCTGTATA
GGGTCTGGAGACATCTCCAGCTTCAATGCCATGGGCTGGTACCGCCAGGTTCCAGGGAAGCAGCGCGAA
TTGGTCGCATTTATTAGTAGCGGTGGTCGCTCAAAATATACAGACTCCGTGAAGGGCCGATTCACCATC
TCCGGAGACAACGCCAAGAACACGGTGTATCTGCAAATGATCGACCTGAAACCTGAGGACACAGCCGTC
TATTACTGTAATGCAGGTTCGGTGGTATCATACGAAACTGGTAATTACTACGAACCATCTAACTACTGG
GGCCAGGGGACCCAGGTCACCGTCTCCTCA $V_H$H C20

(SEQ ID NO: 16)

CAGGTAAAGCTGGAGGAGTCTGGGGGAGGCTTGGTGCAGCCTGGGGGGTCTCTGAGACTCTCCTGTGTA
GGGTCTGGAAGCATCTCCAGCTTCAATGGCATGGGCTGGTACCGCCAGGTTCCAGGGAAGCAGCGCGAA
TTGGTCGCATTTATCAGTAGTGGTGGTCGCTCAAAATATACAGACTCCGTGAAGGGCCGATTCACCATC
TCCGGAGACAACGCCAAGAGCACGGTGTATCTGCAAATGATCAACCTGAAACCTGAGGACACAGCCGTC
TATTACTGTAATGTCGGTTCCGTGCTATCATACGTAACTGGTAATTACTACGAACCATCTGATTACTGG
GGCCAGGGGACCCAGGTCACCGTCTCCTCA $V_H$H C43

(SEQ ID NO: 17)

CGGGTAAAGCTGGAGGAGTCTGGGGGAGGCTTGGTGCAGGCTGGGGGGTCTCTGAGACTCTCCTGTGCT
GTCTCTGGATCTACTTTCGATGATTATGCCATAGGCTGGTACCGCCAGGCTCCAGGGAAGCAGCGCGAA
GTGGTCGCAGTTATTACTAATGGTAATAGTCCAAACTATGCAGACTCCGTGAAGGGCCGATTCACCATC
TCCAGAGACAACGCCAAGAACACGGTGTATTTGCAAATGAACAGCCTGAAACCTGAGGACACGGCCGTC
TATTACTGTAATGTCGAGGGTGTTCGGTACGGTGATAGCTGGTACGATGGTGACTACTGGGGCCAGGGG
ACCCAGGTCACCGTCTCCTCA

Predicted amino acid sequences $V_H$H C2

(SEQ ID NO: 1)

QVKLEESGGGLVLPGGSLRLSGAASGSISSIYAMGWYRQAPGKQREVVAVITNGNSPNYADSVKGRFTI
SRDNAKNTVYLQMNSLKPEDTAVYYCNVEGVRYGDSWYDGDYWGQGTQVTVSS $V_H$H C19

(SEQ ID NO: 2)

QVKLEESGGGLAQAGGSLRLSCIGSGDISSFNAMGWYRQVPGKQRELVAFISSGGRSKYTDSVKGRFTI
SGDNAKNTVYLQMIDLKPEDTAVYYCNAGSVVSYETGNYYEPSNYWGQGTQVTVSS $V_H$H C20

(SEQ ID NO: 3)

QVKLEESGGGLVQPGGSLRLSCVGSGSISSFNIGMGWYRQVPGKQRELVAFISSGGRSKYTDSVKGRFTI
SGDNAKSTVYLQMINLKPEDTAVYYCNVGSVLSYVTGNYYEPSDYWGQGTQVTVSS

TABLE 5-continued

| Nucleotide and Amino Acid Sequences for Anti-α-cobratoxin $V_HH$ C2, C19, C20 and C43. |
|---|
| $V_HH$ C43 |
| (SEQ ID NO: 4) |
| RVKLEESGGGLVQAGGSLRLSCAVSGSTFDDYAIGWYRQAPGKQREVVAVITNGNSPNYADSVKGRFTI |
| SRDNAKNTVYLQMNSLKPEDTAVYYCNVEGVRYGDSWYDGDYWGQGTQVTVSS |

TABLE 6

Identity and Similarity Among Amino Acid Sequences for $V_HH$ C2, C19, C20 and C30.

| | Identity | | | |
|---|---|---|---|---|
| similarity | C2 | C19 | C20 | C43 |
| C2 | 100%/100% | 71% | 73% | 92% |
| C19 | 76% | 100%/100% | 91% | 68% |
| C20 | 79% | 95% | 100%/100% | 69% |
| C43 | 94% | 75% | 76% | 100%/100% |

% identity is shown above the diagonal; % similarity, below.

TABLE 7

Consensus Sequence for $V_HH$ C2, C19, C20 and C30.

```
VHH_C2      QVKLEESGGGLVLPGGSLRLSCAASGSISSIYAMGWYRQAPGKQREVVAVITNGNSPNYA   60
VHH_C43     RVKLEESGGGLVQAGGSLRLSCAVSGSTFDDYAIGWYRQAPGKQREVVAVITNGNSPNYA   60
VHH_C19     QVKLEESGGGLAQAGGSLRLSCIGSGDISSFNAMGWYRQVPGKQRELVAFISSGGRSKYT   60
VHH_C20     QVKLEESGGGLVQPGGSLRLSCVGSGSISSFNGMGWYRQVPGKQRELVAFISSGGRSKYT   60
CONSENSUS   :**********. .********  **.  .  .:*****.******:**.*:.*. .:*:

VHH_C2      DSVKGRFTISRDNAKNTVYLQMNSLKPEDTAVYYCNVEGVR---YGDSWYDGDYWGQGTQ  117
VHH_C43     DSVKGRFTISRDNAKNTVYLQMNSLKPEDTAVYYCNVEGVR---YGDSWYDGDYWGQGTQ  117
VHH_C19     DSVKGRFTISGDNAKNTVYLQMIDLKPEDTAVYYCNAGSVVSYETGNYYEPSNYWGQGTQ  120
VHH_C20     DSVKGRFTISGDNAKSTVYLQMINLKPEDTAVYYCNVGSVLSYVTGNYYEPSDYWGQGTQ  120
CONSENSUS   ********** ****.****** .************ . .*     *: :  .:*******

VHH_C2      VTVSS 122
VHH_C43     VTVSS 122
VHH_C19     VTVSS 125
VHH_C20     VTVSS 125
C           *****
```

Full Citations for References Referred to in the Specification

Arbabi Ghahroudi, M., Desmyter, A., Wyns, L., Hamers, R., Muyldermans, S. 1997. Selection and identification of single domain antibody fragments from camel heavy-chain antibodies. FEBS Lett. 414:521-526.

Bourne, Y., Talley, T. T., Hansen, S. B., Taylor, P., Marchot, P. 2005. Crystal structure of α-Cbtx-AChBP complex reveals essential interactions between snake α-neurotoxins and nicotinic receptors. EMBO J. 24:1512-1522.

Bulbring, E. 1946. Observation on the isolated phrenic nerve-diaphragm preparation of the rat. Br. *J. Pharmacol.* 1: 38-61.

Chippaux, J. P. 1998. Snake-bites: appraisal of the global situation. Bull. World Health Organ. 76:515-524.

Chippaux, J. P. 2006. The Epidemiology of Envenomations. In Snake venoms and envenomations. Translated by F. W. Huchzermeyer. Krieger Publishing Company, Florida. pp. 193.

Chotwiwatthanakun, C., Pratanaphon, R., Akesowan, S., Sriprapat, S., Ratanabanangkoon, K. 2001. Production of potent polyvalent antivenom against three elapid venoms using a low dose, low volume, multi-site immunization protocol. Toxicon. 39: 1487-1494.

Cortez-Retamozo, V., Lauwereys, M., Hassanzadeh, G. H., Gobert, M., Conrath, K., Muyldermans, S., De Baetselier, P., Revets, H. 2002. Efficient tumor targeting by single-domain antibody fragments of camels. Int. J. Cancer. 98:456-462.

Cortez-Retamozo, V., Backmann, N., Senter, P. D., Wernery, U., De Baetselier, P., Muyldermans, S., Revets, H. 2004. Efficient cancer therapy with a nanobody-based conjugate. Cancer Res. 64: 2853-2857.

Frenken, L., van der Linden, R. H. J., Hermans, P. W. J. J. 2000. Isolation of antigen-specific Llama VHH antibody fragment and their high level of secretion by *Saccharomyces cerevisiae.* 78:11-21.

Ghahroudi, M. A, Desmyter, A., Wyns, L., Hamers, R., Muyldermans, S. 1997. Selection and identification of single domain antibody fragments from camel heavy-chain antibodies. FEBS Letters. 414: 521-526.

Gutierrez, J. M., Leon, G., Rojas, G., Lamonte, B., Rucavado, A., Chaves, F. 1998. Neutralization of local tissue damage induced by *Bothrops asper* (terciopelo) snake venom. Toxicon. 36:1529-1536.

Gutierrez, J. M., Rucavado, A. 2000. Snake venom metalloproteinases: Their role in pathogenesis of local tissue damage. Biochimie 82:841-850.

Hamers-Casterman, C., Atarhouch, T., Muyldermans, S., Robinson, G., Hamer, C., Songa, E. B., Bendahman, N.; Hamers, R. 1993. Naturally occurring antibodies devoid of light chains. Nature. 363:446-448.

Harmsen M. M., Ruuls R. C., Nijman I. J., Niewold T. A., Frenken L. G. and de Geus B. 2000. Llama heavy-chain V regions consist of at least four distinct subfamilies revealing novel sequence features. *Mol Immunol* 37, 579-90.

Inoue, S., Ohkura, K., Ikeda, K., Hayashi, K. 1987. Amino acid sequence of a cytotoxin-like basic protein with low cytotoxic activity from the venom of the Thailand cobra *Naja naja siamensis*. FEBS 218:17-21.

Kabat E. A. and Wu T. T. 1991. Identical V region amino acid sequences and segments of sequences in antibodies of different specificities. Relative contributions of VH and VL genes, minigenes, and complementarity-determining regions to binding of antibody-combining sites. *J Immunol* 147, 1709-19.

Karlsson, E. 1979. Chemistry of protein toxins in snake venoms. In Handbook of Experimental Pharmacology. Edited by C. Y. Lee. Springer, Berlin, 52:159-212.

Lalloo, D., Theakston, R. D. 2003. Snake antivenoms. J. Toxicol. Clin. Toxicol. 41:277-290.

Minton, S. A. 1990. Neurotoxic snake envenoming. Semin. Neurol. 10: 52-61.

Muruganandam, A., Tanha, J., Narang, S., Stanimirovic, D. 2002. Selection of phage-displayed llama single-domain antibodies that transmigrate across human blood-brain barrier endothelium. FASEB J. 16: 240-242.

Pratanaphon, R., Akesowan, S., Khow, O., Sriprapat, S., Ratanabanangkoon, K. 1997. Production of highly potent horse antivenom against the Thai cobra (*Naja kaouthia*). Vaccine. 15:1523-1528.

Stewart, C. S., MacKenzie, R. C., Hall, J. C. 2007. Isolation, characterization and pentamerization of α-cobrotoxin specific single-domain antibodies from a naïve phage display library: Preliminary findings for antivenom development. Toxicon. 49: 699-709.

Viravan, C., Veeravat, U., Warrell, M. J., Theakston, R. D., Warrell, D. A. 1986. ELISA confirmation of acute and past envenoming by the monocellate Thai cobra (*Naja kaouthia*). Am. J. Trop. Med. Hyg. 35: 173-181.

Vu, K. B., Ghahroudi, M. A., Wyns, L., Muyldermans, S. 1997. Comparison of llama VH sequences from conventional and heavy chain antibodies. Mol. Immunol. 34: 1121-1131.

---

The invention claimed is:

1. An isolated $V_H$H antibody fragment obtained from a $V_H$H library prepared by a method comprising:

(1) immunizing a camelid with whole venom or an extract thereof;

(2) isolating nucleic acid sequences encoding the variable heavy fragment from the immunized camelid; and (3) transforming a suitable host with the nucleic acid sequences to prepare a recombinant $V_H$H library comprising $V_H$H antibody fragments, wherein the $V_H$H antibody fragments comprise a heavy chain complementarity determining region 1 (CDR1) comprising the amino acid sequence of SEQ ID NO:5; a heavy chain complementarity determining region 2 (CDR2) comprising the amino acid sequence of SEQ ID NO:9; and a heavy chain complementarity determining region 3 (CDR3) comprising the amino acid sequence of SEQ ID NO:11.

2. The isolated $V_H$H antibody fragment according to claim 1 that can bind to one or more proteins in a venom.

3. The isolated $V_H$H antibody fragment according to claim 1, wherein the venom is snake venom.

4. The isolated $V_H$H antibody fragment according to claim 3, wherein the $V_H$H antibody fragment binds to α-cobratoxin.

5. An isolated $V_H$H antibody fragment comprising a heavy chain complementarity determining region 1 (CDR1) comprising the amino acid sequence of SEQ ID NO:5; a heavy chain complementarity determining region 2 (CDR2) comprising the amino acid sequence of SEQ ID NO:9; and a heavy chain complementarity determining region 3 (CDR3) comprising the amino acid sequence of SEQ ID NO:11.

6. An isolated $V_H$H antibody fragment comprising the amino acid sequence of SEQ ID NO:1.

7. A pharmaceutical composition comprising an effective amount of the $V_H$H antibody fragment according to claim 5 in admixture with a suitable diluent or carrier.

8. A kit comprising an effective amount of the $V_H$H antibody fragment according to claim 5 together with ancillary agents and instructions for use thereof.

9. The kit according to claim 8, wherein the instructions for use thereof comprise treating a subject exposed to a venom and/or treating envenomation in a subject and/or neutralizing a venom in a subject that has been exposed to the venom.

10. A pharmaceutical composition comprising an effective amount of the $V_H$H antibody fragment according to claim 6 in admixture with a suitable diluent or carrier.

11. A kit comprising an effective amount of the $V_H$H antibody fragment according to claim 6 together with ancillary agents and instructions for use thereof.

12. The kit according to claim 11, wherein the instructions for use thereof comprise treating a subject exposed to a venom and/or treating envenomation in a subject and/or neutralizing a venom in a subject that has been exposed to the venom.

13. The isolated $V_H$H antibody fragment according to claim 5 that can bind to one or more proteins in a venom.

14. The isolated $V_H$H antibody fragment according to claim 5, wherein the venom is snake venom.

15. The isolated $V_H$H antibody fragment according to claim 5, wherein the $V_H$H antibody fragment binds to α-cobratoxin.

* * * * *